(12) United States Patent
Garlow et al.

(10) Patent No.: US 11,925,494 B2
(45) Date of Patent: *Mar. 12, 2024

(54) SYSTEM AND METHOD FOR MOBILE IMAGING

(71) Applicant: Medtronic Navigation, Inc., Louisville, CO (US)

(72) Inventors: David A. Garlow, Lynnfield, MA (US); Robert P. Cloutier, Lancaster, MA (US); John T. Hickey, Littleton, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/740,534

(22) Filed: May 10, 2022

(65) Prior Publication Data

US 2022/0265232 A1  Aug. 25, 2022

Related U.S. Application Data

(63) Continuation of application No. 16/144,058, filed on Sep. 27, 2018, now Pat. No. 11,344,268.

(Continued)

(51) Int. Cl.
*A61B 6/00* (2006.01)
*A61B 5/055* (2006.01)
(Continued)

(52) U.S. Cl.
CPC ............ *A61B 6/4405* (2013.01); *A61B 5/055* (2013.01); *A61B 6/032* (2013.01); *A61B 6/035* (2013.01);
(Continued)

(58) Field of Classification Search
CPC ....... A61B 6/4447; A61B 5/055; A61B 6/547; A61B 6/467; A61B 6/032; A61B 6/4405;
(Continued)

(56) References Cited

U.S. PATENT DOCUMENTS 5,592,939 A  1/1997  Martinelli
5,913,820 A  6/1999  Bladen et al.
(Continued)

FOREIGN PATENT DOCUMENTS

CN  101027947 A  8/2007
CN  102724914 A  10/2012
(Continued)

OTHER PUBLICATIONS

Neurologica, Body Tom® product brochure, Bringing the power of imaging to your patient, Portable full body 32-slice CT scanner, 12 pages, 2016.
(Continued)

*Primary Examiner* — Irakli Kiknadze
(74) *Attorney, Agent, or Firm* — Harness, Dickey & Pierce, P.L.C.

(57) ABSTRACT

An imaging system is disclosed. The imaging system is operable to acquire and/or generate image data at positions relative to a subject. The imaging system includes a drive system configured to move the imaging system.

20 Claims, 19 Drawing Sheets

Related U.S. Application Data

(60) Provisional application No. 62/565,817, filed on Sep. 29, 2017.

(51) Int. Cl.
*A61B 6/03* (2006.01)
*A61B 6/04* (2006.01)

(52) U.S. Cl.
CPC .......... *A61B 6/4411* (2013.01); *A61B 6/4447* (2013.01); *A61B 6/467* (2013.01); *A61B 6/547* (2013.01); *A61B 6/04* (2013.01); *A61B 6/4435* (2013.01)

(58) Field of Classification Search
CPC ..... A61B 6/035; A61B 6/4411; A61B 6/4435; A61B 6/04; A61B 5/0046; A61B 6/504; A61B 6/508; A61B 6/4452; A61B 6/027; A61B 6/4441; A61B 6/06; A61B 6/466; A61B 6/56; A61B 6/586; A61B 6/03; A61B 6/485; A61B 6/4085; A61B 6/105; A61B 6/4021; A61B 6/54; A61B 5/0555; A61B 6/4266; H05G 1/10; G01R 33/381; H02G 11/006; B60B 19/003
USPC ...................................................... 378/11, 62
See application file for complete search history.

(56) References Cited

U.S. PATENT DOCUMENTS

| | | |
|---|---|---|
| 5,983,126 A | 11/1999 | Wittkampf |
| 6,131,690 A | 10/2000 | Galando et al. |
| 6,474,341 B1 | 11/2002 | Hunter et al. |
| 6,747,539 B1 | 6/2004 | Martinelli |
| 6,940,941 B2 | 9/2005 | Gregerson et al. |
| 7,001,045 B2 | 2/2006 | Gregerson et al. |
| 7,106,825 B2 | 9/2006 | Gregerson et al. |
| 7,108,421 B2 | 9/2006 | Gregerson et al. |
| 7,188,998 B2 | 3/2007 | Gregerson et al. |
| 7,751,865 B2 | 7/2010 | Jascob et al. |
| 7,797,032 B2 | 9/2010 | Martinelli et al. |
| 9,554,953 B2 | 1/2017 | Pirauf et al. |
| 9,737,235 B2 | 8/2017 | Hartmann |
| 10,245,945 B2 | 4/2019 | Xiong et al. |
| 10,448,910 B2 | 10/2019 | Johnson et al. |
| 10,687,770 B2 | 6/2020 | Sullivan et al. |
| 10,842,453 B2 | 11/2020 | Johnson et al. |
| 11,039,964 B2 | 6/2021 | Paul et al. |
| 11,058,378 B2 | 7/2021 | Johnson et al. |
| 11,344,268 B2 * | 5/2022 | Garlow .............. A61B 6/4447 |
| 11,399,784 B2 * | 8/2022 | Garlow .............. A61B 6/4411 |
| 2004/0116803 A1 | 6/2004 | Jascob et al. |
| 2004/0199072 A1 | 10/2004 | Sprouse et al. |
| 2006/0083354 A1 | 4/2006 | Tybinkowski et al. |
| 2010/0064431 A1 | 3/2010 | Kawakami et al. |
| 2012/0104264 A1 * | 5/2012 | Bailey ................ G01N 23/046 250/363.04 |
| 2012/0155616 A1 | 6/2012 | Rijken et al. |
| 2012/0250822 A1 | 10/2012 | Helm et al. |
| 2013/0003939 A1 | 1/2013 | Bouvier et al. |
| 2013/0140801 A1 | 6/2013 | Schlee et al. |
| 2014/0232174 A1 | 8/2014 | Zdrahal et al. |
| 2014/0265182 A1 | 9/2014 | Stanton et al. |
| 2014/0278221 A1 | 9/2014 | Troy et al. |
| 2016/0082596 A1 | 3/2016 | Barth et al. |
| 2016/0270748 A1 | 9/2016 | Garlow |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0325763 A1 | 11/2017 | Hoernig et al. |
| 2018/0043951 A1 | 2/2018 | Jebelhart et al. |
| 2018/0249981 A1 | 9/2018 | Johnson et al. |
| 2018/0317870 A1 | 11/2018 | Fehre et al. |
| 2018/0321684 A1 | 11/2018 | Gao |
| 2019/0023548 A1 | 1/2019 | Jones et al. |
| 2019/0029629 A1 | 1/2019 | Johnson et al. |
| 2019/0150865 A1 | 5/2019 | Johnson et al. |
| 2020/0069268 A1 | 3/2020 | Johnson et al. |
| 2020/0080911 A1 | 3/2020 | Hafenrichter et al. |
| 2020/0085390 A1 | 3/2020 | Johnson et al. |
| 2020/0237588 A1 | 7/2020 | Moore |
| 2020/0367842 A1 | 11/2020 | Limoli et al. |
| 2021/0315531 A1 | 10/2021 | Johnson et al. |

FOREIGN PATENT DOCUMENTS

| | | |
|---|---|---|
| CN | 103260519 A | 8/2013 |
| CN | 103269643 A | 8/2013 |
| CN | 104144845 A | 11/2014 |
| CN | 105009012 A | 10/2015 |
| DE | 102016208123 A1 | 9/2017 |
| EP | 2868277 A1 | 5/2015 |
| JP | 2000287963 A | 10/2000 |
| JP | 2008508061 A | 3/2008 |
| JP | 20120095460 A | 5/2012 |
| JP | 2012110702 A | 6/2012 |
| JP | 2013503778 A | 2/2013 |
| JP | 201381659 A | 5/2013 |
| JP | 2013540535 A | 11/2013 |
| JP | 2016154736 A | 9/2016 |
| WO | 2011067648 A1 | 6/2011 |
| WO | 2017136550 A1 | 8/2017 |

OTHER PUBLICATIONS

Brainlab, AIRO® product brochure, Mobile Intraoperative CT, 10 pages, 2014.
Galil Motion Control, Inc., DMC-18×6 product brochure, 229 pgs, 2016.
Invitation to Pay Additional Fees dated Jan. 25, 2019 in corresponding/related International Application No. PCT/US2018/053438.
International Search Report and Written Opinion dated Mar. 20, 2019 in corresponding/related International Application No. PCT/US2018/053438.
International Preliminary Report on Patentability dated Apr. 9, 2020 in corresponding/related International Application No. PCT/US2018/053438.
Office Action regarding Australian Patent Application No. 2017258292 dated Apr. 19, 2021.
Japanese Office Action regarding Application No. 202051503.2, dated Feb. 18, 2022. .
U.S. Appl. No. 16/144,058, filed Sep. 27, 2018, David A. Garlow et al.
U.S. Appl. No. 16/144,058, 2019-0099140, filed Sep. 27, 2018, David A. Garlow et al.
U.S. Appl. No. 16/144,103, 2019-0099141, filed Sep. 27, 2018, David A. Garlow et al.
Japanese Office Action regarding Patent Application No. 2020515032, dated Sep. 29, 2022.
Chinese 1st Office Action, corresponding to CN 201880062742.3, dated Feb. 28, 2023, and China National Intellectual Property Administration Search Report.
Korean Office Action, corresponding to Korean Patent Application No. 10-2020-7011067, corresponding to PCT/US2018/053438, dated Feb. 9, 2023.
Examination Report corresponding to European Application No. 18788967.0, dated Jul. 18, 2023 (4 pp).
Chinese 2nd Office Action corresponding to Chinese Application No. 201880062742.3 dated Nov. 28, 2023, 20 pages.

* cited by examiner

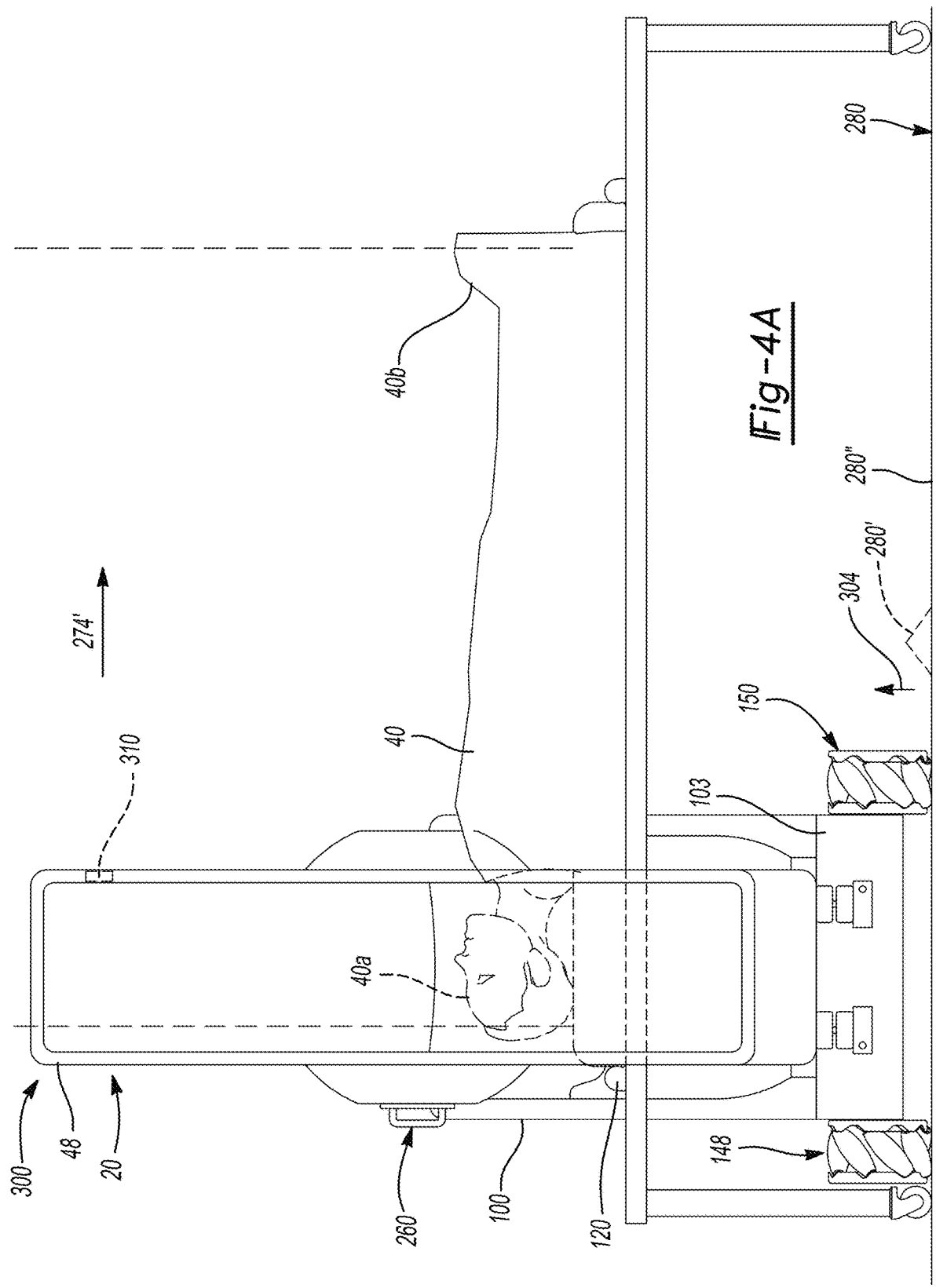

SYSTEM AND METHOD FOR MOBILE IMAGING

CROSS-REFERENCE TO RELATED APPLICATIONS

This application is a continuation of U.S. patent application Ser. No. 16/144,058 filed Sep. 27, 2018, which claims the benefit of U.S. Provisional Application No. 62/565,817, filed on Sep. 29, 2017, entitled "SYSTEM AND METHOD FOR MOBILE IMAGING". This application includes subject matter similar to U.S. patent application Ser. No. 16/144,103 filed Sep. 27, 2018. The entire disclosures of the above applications are incorporated herein by reference.

FIELD

The subject disclosure is related to an imaging system, and particularly a mobile imaging system.

BACKGROUND

This section provides background information related to the present disclosure which is not necessarily prior art.

Imaging systems generally include integrated patient supports that are used during an imaging procedure. Generally known imaging systems include the BodyTom® CT Imaging System sold by Neurologica Corp. and the Airo® CT Imaging System sold by Brain Lab. These imaging systems include patient supports that are custom designed to hold the patient and provide a track for rigid movement of the imaging system relative to patient support. Imaging systems may further include bases that are fixed in place and include a gantry that is able to move a short distance, such as about 12 centimeters to about 18 centimeters relative to the base during imaging. The generally known imaging systems may, therefore, include limited mobility other than relative to the patient support.

SUMMARY

This section provides a general summary of the disclosure, and is not a comprehensive disclosure of its full scope or all of its features.

A system for acquiring image data of a subject, also referred to as an imaging system, is disclosed. The imaging system may acquire image data that is used to generate images of various types. The images may include reconstructed three-dimensional images, two-dimensional images, or other appropriate image types. In various embodiments, the imaging system may be an X-ray scanner or a CT scanner. The image data may be two-dimensional (e.g. projection image data) or other appropriate types of image data.

The imaging system may further include a mobility feature that allows it to move relative to a subject. In various embodiments, the subject may be positioned on a support, such as a standard and/or generally known radiolucent surgical table such as the STERIS 4085 SURGICAL TABLE sold by Steris plc, having a place of business in Ohio, that is generally located in selected medical facilities. The imaging system is configured to be positioned relative to the subject to acquire image data of the subject in a selected manner to allow reconstruction of images for display of selected images.

In various embodiments, image data may be acquired while the imaging system is moving relative to the subject. For example, the imaging system may rotate in all or a portion of 360 degrees relative to (e.g. around) the subject. The imaging system may, also or in addition to rotation, move along a longitudinal axis of the subject. In moving along the longitudinal axis of the subject and/or transverse to the longitudinal axis, the imaging system may be driven by a drive system that may include selected wheel supports. The wheel supports may include omni-directional wheels, such as mecanum or omni-wheels. The omni-directional wheels generally include at least a first rolling portion and a second roller or rolling portion. The imaging system may move substantially in one or both of an X-axis and a Y-axis direction. Further, the imaging system may tilt relative to the subject to acquire image data at an angle relative to the longitudinal axis of the subject.

The imaging system may be moved by a manual manipulation of the imaging system. In various embodiments, the imaging system may include a handle that includes one or more sensors that sense a force, such as pressure, from the user to directly move the imaging system relative to the subject. The manual movement of the imaging system may be inclusive or exclusive of other drive or robotic control features of the imaging system. Accordingly, the user may selectively move the imaging system relative to the subject in an efficient and quick manner without pre-planning a movement of the system.

The imaging system may further include controls, such as automatic or robotic controls, that move the imaging system relative to the subject. The imaging system may move with or according to a pre-planned path relative to the subject for acquiring a selected image data collection of the subject. For example, reconstruction of a selected three-dimensional model of a selected portion of the subject may be selected, and the imaging system may be programmed to automatically move relative to the subject to acquire appropriate amount and type of image data for the three-dimensional reconstruction.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4A is a schematic view of the imaging system in a first position;

Corresponding reference numerals indicate corresponding parts throughout the several views of the drawings.

DETAILED DESCRIPTION

Example embodiments will now be described more fully with reference to the accompanying drawings.

Figure 1:
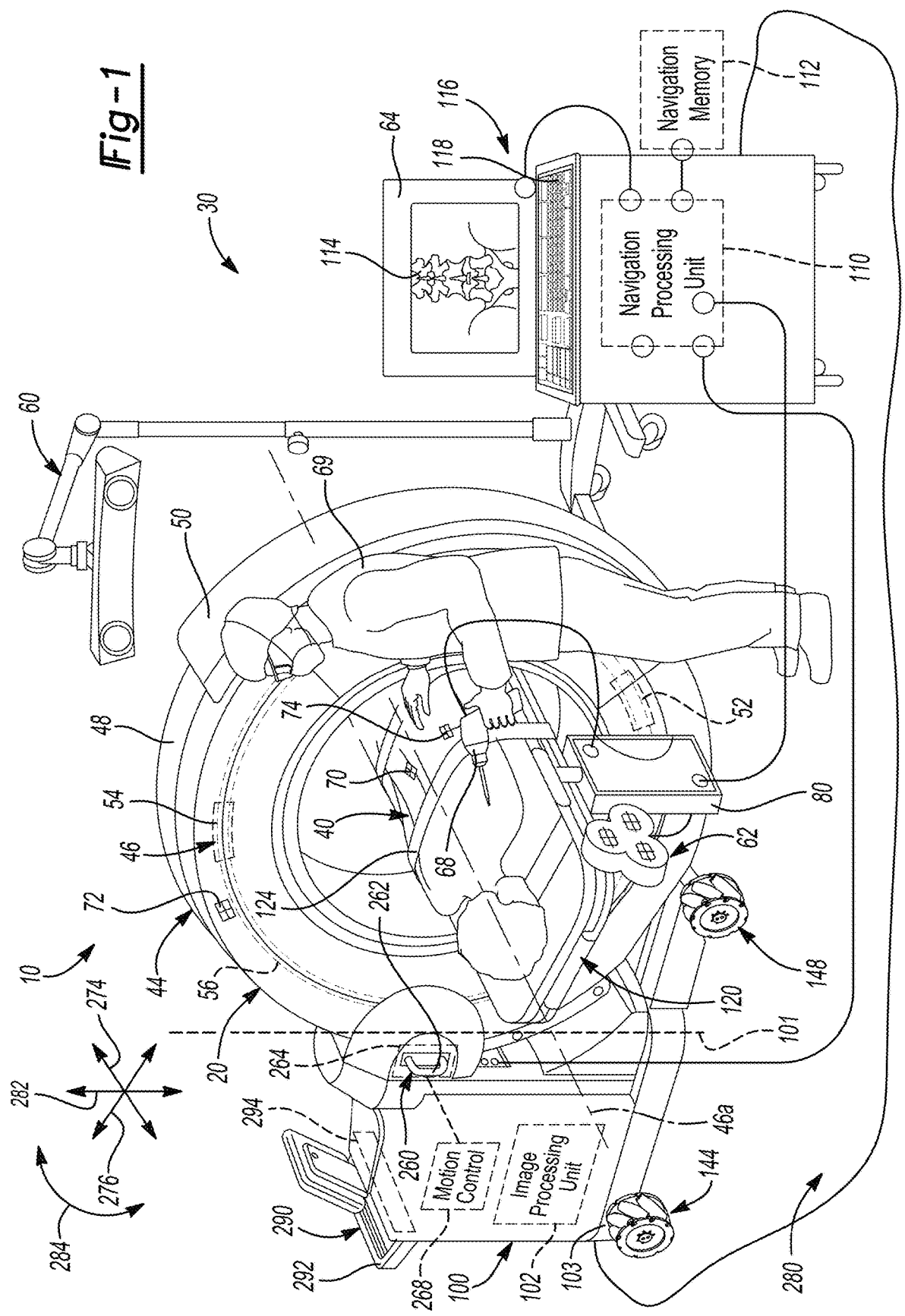
FIG. 1 is an environmental view of an imaging system.

FIG. 1 is a diagram illustrating an overview of an operating theater system 10 that may include an imaging system 20 and a navigation system 30, which can be used for various procedures. The navigation system 30 can be used to track the location of an item, such as an implant or an instrument, relative to a subject, such as a patient 40. It should further be noted that the navigation system 30 may be used to navigate any type of instrument, implant, or delivery system, including: guide wires, arthroscopic systems, orthopedic implants, spinal implants, deep brain stimulation (DBS) probes, etc. Moreover, the instruments may be used to navigate or map any region of the body. The navigation system 30 and the various tracked or navigated items may be used in any appropriate procedure, such as one that is generally minimally invasive or an open procedure.

The navigation system 30 can interface with the imaging system 20 that is used to acquire pre-operative, intra-operative, or post-operative, or real-time image data of the patient 40. It will be understood, however, that any appropriate subject can be imaged and any appropriate procedure may be performed relative to the subject. In the example shown, the imaging system 20 comprises or may include portions of an O-Arm® imaging system or device sold by Medtronic Navigation, Inc. having a place of business in Louisville, Colorado, USA. In various embodiments, the imaging system 20 may have a gantry housing 44 that encloses an image data capturing portion 46. The gantry 44 may include a first portion 48 (which may include a generally fixed portion) and a second portion 50 (which may include a moveable portion relative to the first portion 48). The image capturing portion 46 may include an x-ray source or emission portion 52 and an x-ray receiving or image receiving portion (also referred to as a detector that may be operable to detect x-rays) 54 located generally or as practically possible 180 degrees from each other and mounted on a moveable rotor (not illustrated) relative to a track 56 of the image capturing portion 46. The image capturing portion 46 can be operable to rotate 360 degrees around the gantry 44 on or with the rotor during image data acquisition.

The image capturing portion 46 may rotate around a central point or axis 46a, allowing image data of the patient 40 to be acquired from multiple directions or in multiple planes. The axis 46a of the imaging system 20 may be aligned or positioned relative to an axis, such as a longitudinal axis, of the patient 40. The imaging system 20 can include all or portions of the systems and methods those disclosed in U.S. Pat. Nos. 7,188,998; 7,108,421; 7,106,825; 7,001,045; and 6,940,941; all of which are incorporated herein by reference. Other possible imaging systems can include C-arm fluoroscopic imaging systems which can also generate three-dimensional views of the patient 40.

The position of the image capturing portion 46 can be precisely known relative to any other portion of the imaging device 20. In addition, as discussed herein, the precise knowledge of the position of the image capturing portion 46 can be used in conjunction with the navigation system 30 having a tracking portion (e.g. an optical tracking system including an optical localizer 60 and/or an electromagnetic (EM) tracking system including an EM localizer 62) to determine the position of the image capturing portion 46 and the image data relative to the tracked subject, such as the patient 40.

Various tracking devices, including those discussed further herein, can be tracked with the navigation system 30 and the information can be used to allow for displaying on a display 64 of a position of an item, e.g. a tool or instrument 68. The instrument may be operated, controlled, and/or held by a user 69. The user 69 may be one or more of a surgeon, nurse, welder, etc. Briefly, tracking devices, such as a patient tracking device 70, an imaging device tracking device 72, and an instrument tracking device 74, allow selected portions of the operating theater to be tracked relative to one another with the appropriate tracking system, including the optical localizer 60 and/or the EM localizer 62. Generally, tracking occurs within a selected reference frame, such as within a patient reference frame.

It will be understood that any of the tracking devices 70, 72, 74 can be optical or EM tracking devices, or both, depending upon the tracking localizer used to track the respective tracking devices. It is understood that the tracking devices 70-74 may all be similar or different, and may all be interchangeable but selected or assigned selected purposes during a navigated procedure. It will be further understood that any appropriate tracking system can be used with the navigation system 30. Alterative tracking systems can include radar tracking systems, acoustic tracking systems, ultrasound tracking systems, and the like.

An exemplarily EM tracking system can include the STEALTHSTATION® AXIEM™ Navigation System, sold by Medtronic Navigation, Inc. having a place of business in Louisville, Colorado Exemplary tracking systems are also disclosed in U.S. Pat. No. 7,751,865, issued Jul. 6, 2010; U.S. Pat. No. 5,913,820, issued Jun. 22, 1999; and U.S. Pat. No. 5,592,939, issued Jan. 14, 1997, all herein incorporated by reference.

Further, for EM tracking systems it may be necessary to provide shielding or distortion compensation systems to shield or compensate for distortions in the EM field generated by the EM localizer 62. Exemplary shielding systems include those in U.S. Pat. No. 7,797,032, issued Sep. 14, 2010 and U.S. Pat. No. 6,747,539, issued Jun. 8, 2004; distortion compensation systems can include those disclosed in U.S. patent application Ser. No. 10/649,214, filed on Jan. 9, 2004, published as U.S. Pat. App. Pub. No. 2004/0116803, all of which are incorporated herein by reference.

With an EM tracking system, the localizer 62 and the various tracking devices can communicate through an EM controller 80. The EM controller can include various amplifiers, filters, electrical isolation, and other systems. The EM controller 80 can also control the coils of the localizer 62 to either emit or receive an EM field for tracking. A wireless communications channel, however, such as that disclosed in U.S. Pat. No. 6,474,341, issued Nov. 5, 2002, herein incorporated by reference, can be used as opposed to being coupled directly to the EM controller 80.

It will be understood that the tracking system may also be or include any appropriate tracking system, including a STEALTHSTATION® TRIA®, TREON®, and/or S7™ Navigation System having an optical localizer, similar to the optical localizer 60, sold by Medtronic Navigation, Inc. having a place of business in Louisville, Colorado. Further alternative tracking systems are disclosed in U.S. Pat. No. 5,983,126, issued Nov. 9, 1999, which is hereby incorporated by reference. Other tracking systems include an acoustic, radiation, radar, etc. tracking or navigation systems.

Briefly, to be discussed in further detail herein, the imaging system 20 can include a support system including a housing or cart 100. The imaging system 20 can further include a separate image processing unit 102 that can be housed in the cart 100. The navigation system 30 can include a navigation processing unit 110 that can communicate or include a navigation memory 112. The navigation processing unit 110 can receive information, including image data, from the imaging system 20 and tracking information from the tracking system, including the respective tracking devices 70, 72, and 74 and the localizers 60, 62. Image data can be displayed as an image 114 on the display device 64 of a workstation or other computer system 116. The workstation 116 can include appropriate input devices, such as a keyboard 118. It will be understood that other appropriate input devices can be included, such as a mouse, a foot pedal or the like.

The image processing unit 102 may be configured, if provided, to process image data from the imaging system 20 and transmit the image data to the navigation processor 110. It will be further understood, however, that the imaging system 20 need not perform any image processing and the image processing unit 102 can transmit the image data directly to the navigation processing unit 110. Accordingly, the navigation system 30 may include or operate with a single or multiple processing centers or units that can access single or multiple memory systems based upon system design. It is understood, however, that all of the processing units discussed herein may be generally processors that are executing instructions recalled form a selected memory, have onboard memory, or be application specific processors. Further, each of the processors may be provided or configured to perform all processing tasks discussed herein. Thus, although a specific process may be discussed as an imaging process, the navigation processing unit 110 may also be configured to perform the process.

The imaging system 20, as discussed herein, may move relative to the patient 40. The patient 40 may be fixed to an operating table or support table 120, but is not required to be fixed to the table 120. The table 120 can include a plurality of straps 124. The straps 124 can be secured around the patient 40 to fix the patient 40 relative to the table 120. Various additional or alternative apparatuses may be used to position the patient 40 in a static position on the operating table 120. Examples of such patient positioning devices are set forth in U.S. Pat. App. Pub. No. 2004/0199072, published Oct. 7, 2004, (U.S. patent application Ser. No. 10/405,068 entitled "An Integrated Electromagnetic Navigation And Patient Positioning Device", filed Apr. 1, 2003), which is hereby incorporated by reference. Other known apparatuses may include a Mayfield® clamp.

Also, the position of the patient 40 relative to the imaging system 20 can be determined by the navigation system 30 with the patient tracking device 70 and the imaging system tracking device 72. Accordingly, the position of the patient 40 relative to the imaging system 20 can be determined. An exemplary imaging system, such as the O-Arm® may also be operated to know a first position and can be repositioned to the same first position within a selected tolerance. The tolerance may be about 0.01 millimeters (mm) to about 10 mm, about 0.01 mm to about 2 mm, and about 10 microns. This allows for a substantially precise placement of the imaging system 20 and precise determination of the position of the imaging device 20. Precise positioning of the imaging portion 22 is further described in U.S. Pat. Nos. 7,188,998; 7,108,421; 7,106,825; 7,001,045; and 6,940,941; all of which are incorporated herein by reference.

Physical space of and/or relative to the subject, such as the patient 40, may be referred to as subject or patient space. Image space of an image or coordinate system of an image that is generated or reconstructed with the image data from the imaging system 30 may be referred to as image space. The image space can be registered to the patient space by identifying matching points or fiducial points in the patient space and related or identical points in the image space. The imaging device 20 can be used to generate image data at a precise and known position. This can allow image data that is automatically or "inherently registered" to the patient 40 upon acquisition of the image data. Essentially, the position of the patient 40 is known precisely relative to the imaging system 20 due to the accurate positioning of the imaging system 20 in the patient space. This allows points in the image data to be known relative to points of the patient 40 because of the known precise location of the imaging system 20.

Alternatively, manual or automatic registration can occur by matching fiducial points in image data with fiducial points on the patient 40. Registration of image space to patient space allows for the generation of a translation map between the patient space and the image space. According to various embodiments, registration can occur by determining points that are substantially identical in the image space and the patient space. The identical points can include anatomical fiducial points or implanted fiducial points. Exemplary registration techniques are disclosed in U.S. Pat. No. 9,737,235, issued Aug. 22, 2017, incorporated herein by reference.

Once registered, the navigation system 30, with and/or including the imaging system 20, can be used to perform selected procedures. Selected procedures can use the image data generated or acquired with the imaging system 20. Further, the imaging system 20 can be used to acquire image data at different times relative to a procedure. As discussed herein, image data can be acquired of the patient 40 subsequent to a selected portion of a procedure for various purposes, including confirmation of the portion of the procedure.

With continuing reference to FIG. 1 and additional reference to FIG. 2, FIG. 3, FIG. 4A, and FIG. 4B, the imaging system 20 may be configured to acquire image data that is used to generate actual or virtual three dimensional images of the patient 40. As discussed above, the imaging system processor 102 and/or the navigation system processing unit 110 may be used to generate or reconstruct images for display and/or viewing by a user 69. The image data is acquired with the patient 40 placed relative to the imaging system 20 to allow the imaging system 20 to obtain image data of the patient 40. While acquiring the image data, the imaging system 20 may move relative to the patient 40.

In various embodiments, to generate a 3D image for display with the display device 64, image data can be acquired from a plurality of views or positions relative to the patient 40. The acquired image data may include a plurality of projections through the patient 40, such as those generated with x-rays, and may include 2D projections. The plurality of projections, or other appropriate image data, of the patient 40 can be used alone or with other information to generate or reconstruct an image to assist in performing a procedure on the patient 40. It is understood, however, that the patient 40 need not be the subject and other appropriate subjects may be imaged. It will also be understood that any appropriate imaging system can be used, including a magnetic resonance imaging (MRI) system, computed tomography (CT) imaging system, fluoroscopy imaging system, X-ray imaging system, etc.

To acquire the plurality of image data, including the plurality of projections of the patient, the imaging system 20 is moved. In various embodiments, the imaging system 20 includes a drive assembly 140 to move and/or assist in movement of the imaging system 20. The drive system 140, as discussed herein, may be a multi-directional drive system, in various embodiments the drive system may be an omni-directional drive system. A multi-directional and/or omni-directional drive system may be configured to move a construct, such as the imaging system 20, in at least two directions separately and/or simultaneously. When moving, for example, the imaging system 20 may be driven by the multi-directional drive system 140 at an angle relative to 2 perpendicular axes. The multi-directional drive system 140 may be operated to rotate the imaging system 20 around an axis 101 defined within the imaging system 20. Moreover, the multi-directional drive system 140 may be operable to drive the imaging system 20 in a plurality of axes while acquiring image data of the subject 40. Further, in various embodiments, the drive system 140 may be operated to move the imaging system in at least two axes of motion simultaneously or separately. It is understood, however, the drive system may move the imaging system 20 in more or less than two axes simultaneously.

The drive system 140 includes wheels or rollers, including at least one (e.g. a first) omni-directional wheel 144. The omni-directional wheel 144, which may include rollers, may translate in a plane and rotate around an axis perpendicular to the plane. During translation, the omni-directional wheel 144 may generally move in any direction from a starting point. Further, the translation and rotation of the omni-directional wheel may be substantially precise and controlled. It is understood that the drive assembly 140 may include more than the omni-directional wheel 144 and may include at least three or more omni-directional wheels. Each of the multiple wheels may be positioned at selected locations relative to one another to be driven to achieve a selected movement of the imaging system 20.

Each of the omni-directional wheels may be substantially similar, however, and include similar or identical portions. The wheels, therefore, may include a second omni-directional wheel 146, a third omni-directional wheel 148 and a fourth omni-directional wheel 150. The omni-directional wheels 144, 146, 148, 150 may be any appropriate omni-directional wheels such as the heavy duty Mecanum Wheel (Item number NM254 AL. manufactured by Omni Mechanical Technology, No. 3 Yaxin Alley, Xiao Bian S T, Chang'an Town, Dongguan City, Guang Dong Province, China).

The use of omni-directional wheels may include operation to drive one or more in a selected manner to move the imaging system 20. For example, two pairs of the wheels could be positioned at corners of a diamond relative to the base 103. One pair could be driven to move the imaging system in a first direction and the other pair could be driven to move the imaging system 20 substantially orthogonal to the first direction. Alternatively, one of each pair could be driven to rotate the imaging system 20. Accordingly, one skilled in the art will understand that the imaging system 20 may be moved in a selected manner by selectively driving one or more of the omni-directional wheels. As discussed herein, the driving of the wheels 144-150 may be used to achieve a selected image data acquisition of the patient 40.

Figure 2:
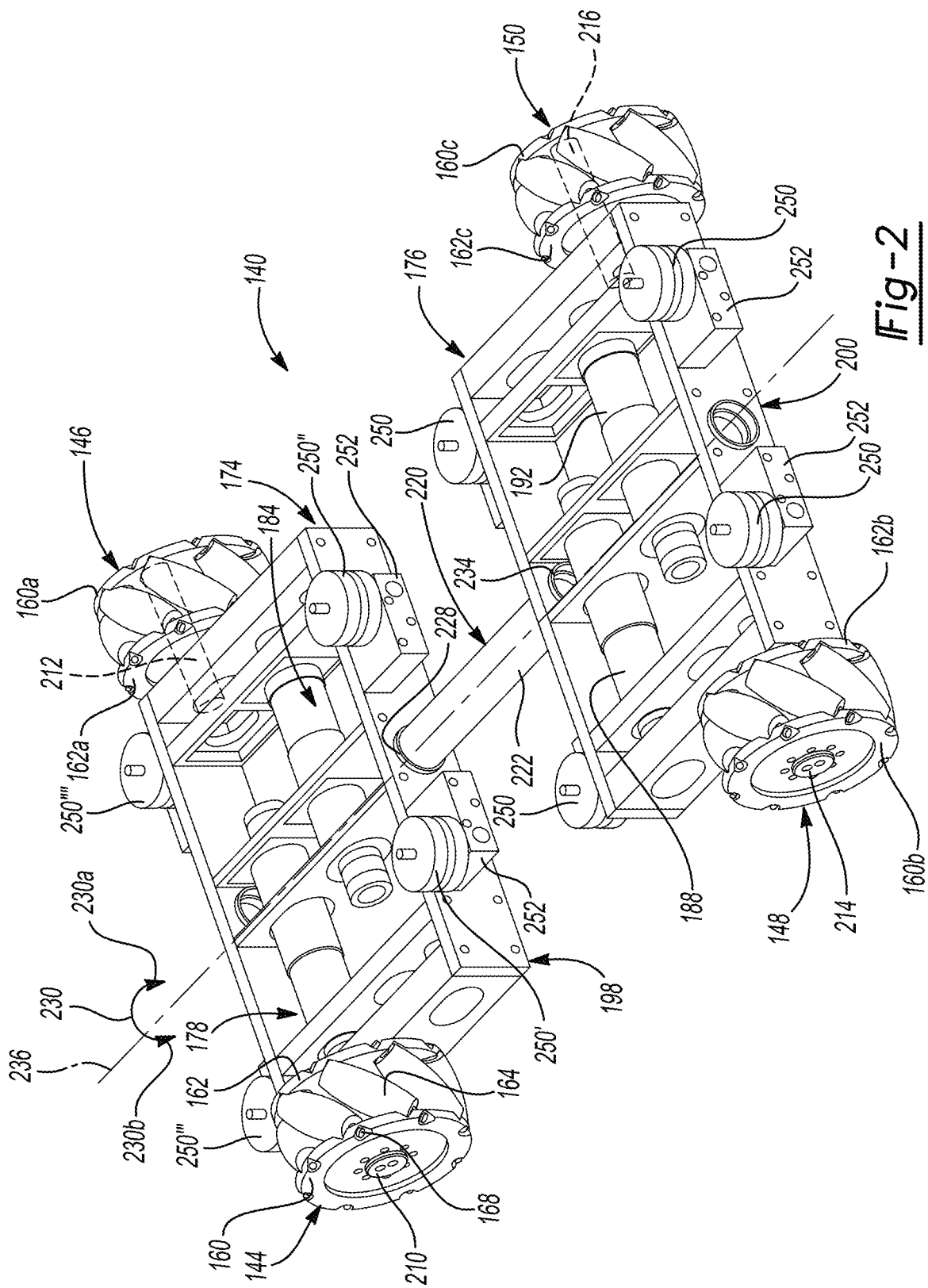
FIG. 2 is a detail view of a drive system.

The omni-directional wheels 144, 146, 148, 150, with reference to FIG. 2, including the first omni-directional wheel 144 may include a plurality of components. For example, the omni-directional wheel 144 may include two external plates, including a first external plate 160 and a second external plate 162. A roller 164 and/or a plurality of rollers may be positioned at an angle relative to a plane of the plate 160 and/or the second plate 162. The roller 164 may be provided to rotate on an axle 168 that is fixedly or rotatably connected to the two end plates 160, 162. In various embodiments, the axles 168 is fixed and the roller 164 rotates around the axles 168.

Figure 3:
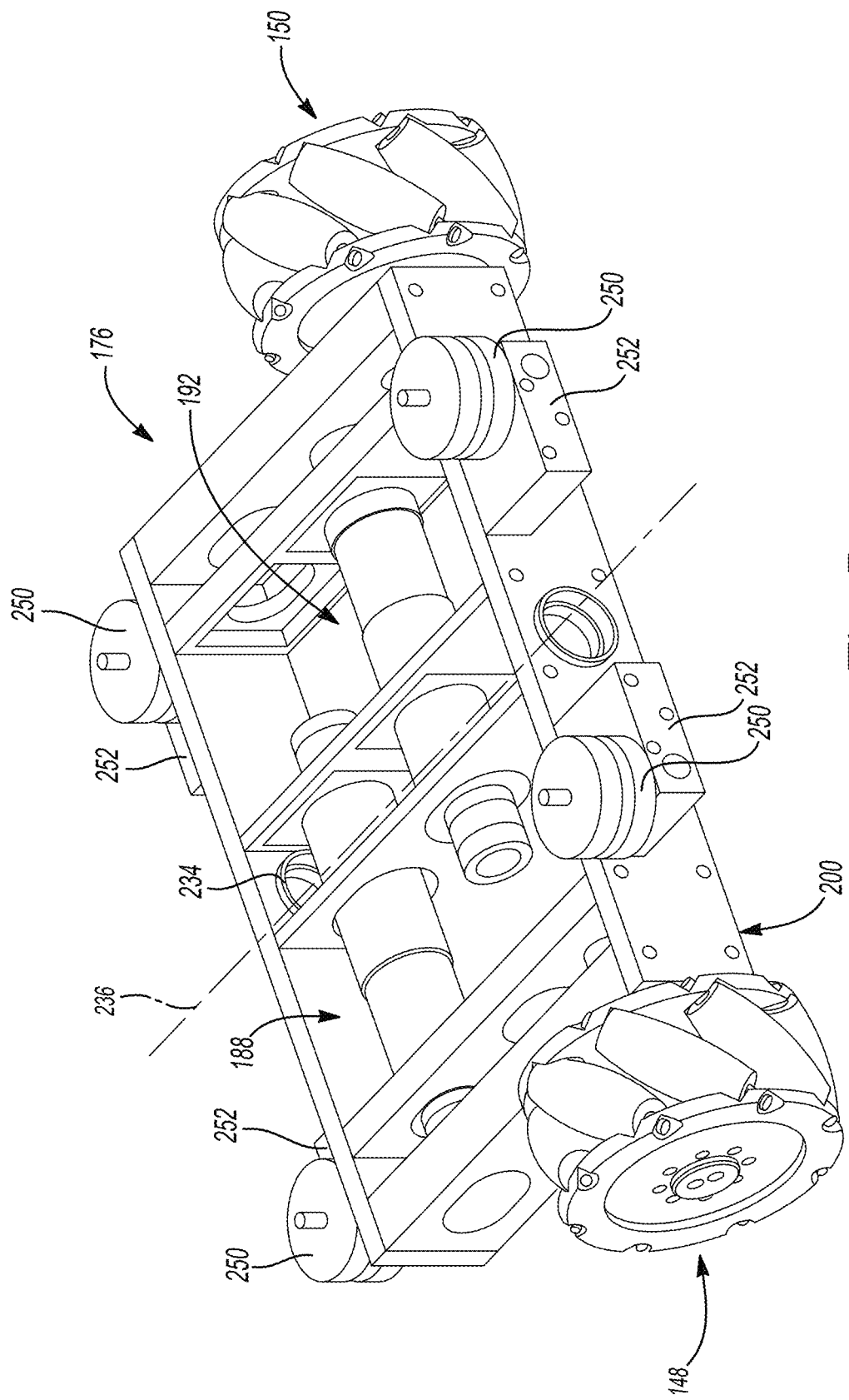
FIG. 3 is a detail view of a drive sub-system of the drive system.

With continuing reference to FIG. 2 and FIG. 3, the drive assembly 140 may be formed or provided as two drive sub-assemblies, including a first drive sub-assembly 174 and a second drive sub-assembly 176. Each of the drive sub-assemblies 174, 176 may be substantially identical, but may be controlled substantially or relatively independently, as discussed herein, to move the imaging system 20. In particular, each of the drive sub-assemblies may include two of the omni-directional wheels 144, 146, 148, 150. For example, the second drive sub-assembly 176 may include the third omni-directional wheel 148 and the fourth omni-directional wheel 150.

Each of the omni-directional wheels 144, 146, 148, 150 may be driven by a respective individual motor including a first motor 178 to drive the first omni-directional wheel 144, a second motor 184 to drive the second omni-directional wheel 146, a third motor 188 to drive the third omni-directional I wheel 148, and a fourth motor 192 to drive the fourth omni-directional wheel 150. The respective motors 178-192 may directly drive their respective omni-directional wheels 144-150, according to various embodiments. It is understood, however, that each of the respective motors 178-192 may indirectly drive their respective wheels 144-150. In various embodiments, as illustrated in FIG. 2 and FIG. 3, a belt drive or chain drive, or other appropriate indirect drive, may interconnect the motors 178-192 with the respective omni-directional wheels 144-150. It is understood that various other interconnection portions may include tensioners, pulleys, and the like to drive the respective omni-directional wheels 144-150 from the respective motors 178-192. It is further understood, however, that the wheels may be drive by direct or indirect drive from the respective motors. Further, a disconnect between the wheels 144-150 and the respective motors 178-192 may be provided, as discussed herein.

Each of the omni-directional wheels 144, as noted above, includes the outer plates 160, 162, as illustrated with respect to the first omni-directional wheel 144. Each of the other wheels 146-150 may include respective outer plates referenced by similar reference numerals augmented by lower case letters.

Each of the drive sub-assemblies 174, 176 include a framework or frame structure such as a first frame 198 of the first drive sub-assembly 174 and a second frame 200 of the second drive sub-assembly 176. Each of the frames 198, 200 may be formed as a single member or multiple members connected together. Further, the frames 198, 200 may include substantially only internal cross-supports and/or a skeletonized framework with no external boundary members. The frames 198, 200 hold the respective drive mechanisms, such as the respective motors 178-192 and the various direct and indirect drive members for the respective omni-directional wheels 144-150.

In various embodiments, a wheel axle 210 extends through the first omni-directional wheel 144 and interconnects with the frame 198. The axle 210 is connected to the omni-directional wheel 144 to allow rotation of the omni-directional wheel 144 relative to the frames 198, 200. For example, the axle 210 may be connected to either or both of the end plates 160, 162 to rotate the omni-directional wheel 144 when driven by the motor 178. Rotating the axle 210 rotates the outer plates 160, 162 to provide motive force to the omni-directional wheel 144.

Each of the other wheels 146-150 may include respective axles such as a second axle 212 for the second omni-directional wheel, a third axle 214 of the third omni-directional wheel 148 and a fourth axle 216 of the fourth wheel 150. Each of the respective axles 210-216 may be driven by the respective motors 178-192 with the respective drive or transmission mechanisms, as discussed above. Driving of the omni-directional wheels 144-150 in a selected manner, as discussed further herein, may move the imaging system 20.

The drive assembly 140, including the first drive sub-assembly 174 and the second drive sub-assembly 176 may be interconnected with a linkage 220. The linkage 220 may be any appropriate linkage, such as a rigid member, including a rigid tubular and/or solid cylindrical member, or other appropriate linkage member. In various embodiments, the linkage 220 includes a substantially cylindrical configuration having an exterior curved surface 222. The linkage 220 may be movably connected to the respective drive sub-assemblies 174, 176 at the respective frames 198, 200.

For example, the first frame 198 may include a linkage connection 228. The linkage connection 228 may include a bearing or bushing that allows the linkage 220 to move relative to the framework 198 or the framework 198 relative to the linkage 220. In various embodiments, the framework 198 may rotate around the linkage 220 generally in the direction of double-headed arrow 230. Similarly the linkage 220 may be connected to the second drive sub-assembly 176 at a second linkage connection 234 of the frame 200. Again the linkage 220 and/or the frame assembly 220 may generally move in the direction of double-headed arrow 230 relative to one another via a pushing and/or bearing at the linkage connection 234.

Accordingly, the drive sub-assembly 174 may move relative to the second drive sub-assembly 176. In other words, the second drive sub-assembly 176 may move in a first direction, such as in the direction of arrowhead 230a, while the first drive sub-assembly 174 moves in the direction of arrowhead 230b. The linkage 220, therefore, and the respective moveable connections 228, 234 allow for the drive sub-assemblies 174, 176 to move independently relative to one another generally around the linkage 220 and an axis 236. As discussed herein, this movement of the drive sub-assemblies 174, 176 relative to one another allows for a selected movement of the imaging system 20 for acquiring image data of the patient 40. This may also, as also discussed further herein, eliminate or reduce vibration or motion of the imaging system 20 relative to the patient 40 during the acquisition of the image data.

One or more shock absorbers (also referred to as cushioning or soft mounts) 250 may be provided to connect to the imaging system 20 to the drive assembly 140. For example, a plurality of the mounts 250 may be provided on the drive assembly 140 either on the frames 198 or projections 250. The projections may be integral or added with an outer surface of a frame member of the frame 198, 200. It is understood that the platforms 252 may be formed with the frames 198, 200 and need not be a separate member, and are illustrated and discussed herein as separate components merely for illustration. Accordingly, the mounts 250 may be provided at any appropriate location of the drive assembly 140 to connect with the imaging system 20.

In various embodiments the mounts 250 may be formed of a resilient and/or compliant material, such as a natural or synthetic rubber, metal spring coil, hydraulic shock absorber, or the like. The mounts 250 allow for cushioning and reduction of vibration or elimination of vibration during movement of the drive assembly 140 relative to the imaging system 20. Accordingly, the drive assembly 140 may move over a surface, such as a floor, pavement, or the like while being non-rigidly connected to the imaging system 20. The mounts 250 allow for a reduction of a force directed or transferred to the imaging system 252 such as by damping or absorbing a force or motion experienced by the drive assembly 140 during motion of the drive assembly 140. The motion may be due to an inconsistency or an unevenness over which the surface of the drive assembly 140 moves or may move due to motion of the drive assembly 140. For example, one or more of the motors 178-192 may cause a shocking or jerking motion during an operation which may be absorbed by the respective mount 250 to thereby eliminate or reduce motion affecting the imaging system 200. The mounts 250 may move or compress a selected amount to allow for suspension of the imaging system 20 in a substantially flat manner during imaging, such as movement of the imaging system 20 during imaging. In various embodiments, however, it is understood that the drive assembly 140 may be rigidly connected to the cart 100. Further, the linkage 220 may not be required between the drive sub-systems 174, 176.

Nevertheless, in various embodiments, the mounts 250 provide articulation about the linkage 220. For example, with discussion relative to the first sub-assembly 174, only two of the mounts 250' and 250" are compliant and the other two mounts 250'" and 250"" are rigidly attached. In this example, the wheels 144, 146 float and this creates a three point contact (the left rear, the right rear and the floating front assembly). Since three points define a plane, the base 103 remains relatively stationary relative to the floor 280. In another example, all of the mounts 250 are compliant and the sub-assembly 174 in total acts similar to an independent suspension to adapt to the terrain and maintain the imaging system 20 relative stationary relative to the floor 280.

Returning reference to FIG. 1 and continuing reference to FIGS. 2 and 3, the imaging system 20 may be positioned by the user 69, or other appropriate individual. In various embodiments, a handle or manipulation assembly 260 is connected with at least a portion, such as a housing or the mobile cart 100 to move the imaging system 20. The user 69 may engage the handle assembly 260 that includes a grasping portion 262 and a sensing portion 264. The handle portion 262 may be connected with one or more sensors in the sensing portion 264 to sense a force, such as an amount of force and a direction of force applied to the handle 262. Other appropriate sensors may be included, such as a flexure, pressure sensor, or the like. In addition, other controls may be provided at the handle assembly 260. The handle assembly 260 may include portions similar to those included in the O-Arm® imaging system sold by Medtronic, Inc. and/or those disclosed in U.S. Pat. App. Pub. No. 2016/0270748, published Sep. 22, 2016, incorporated herein by reference.

In various embodiments, the handle 262 having a force applied thereto by the user 69 and the sensing unit 264 sensing the force applied by the user 69 to the handle 262 may then move the imaging system 20. The sensors in the sensing unit 264 may be any appropriate sensor, such as force sensors (e.g. resistance sensors, voltage sensors, load sensors, position sensors, velocity sensors or the like), direction sensors (e.g. gyroscopes), or other appropriate sensors. The sensors in the sensing unit 264 may send a sense signal to a controller, such as included with the image processing unit 102 and/or a separate motion controller 268. The motion control 268 may receive the sensed signals from the sensors 264 regarding the force applied by the user 69 on the handle 262. The motion controller 268 may then generate a drive signal to drive one or more of the motors 178-192. The motion controller 268 may be any appropriate motion controller, such as multi-axis motion controllers including Ethernet or computer card (PCI) controllers including the DMC-18×6 motion controller sold by Galil Motion Control, having a place of business in Rockland, California.

The motion controller 268, however, may be any appropriate motion controller, and may control the operation of the motors 178-192 to drive the respective wheels 144-150. By controlling the respective motors 178-192, the respective omni-directional wheels 144-150 may be rotated around the respective axles 210-216 in an appropriate manner. By driving the omni-directional wheels 144-150 around the respective axles 210-216 in a selected, manner the imaging system 20 may be moved in or along selected and/or appropriate axes.

Movement of the imaging system, such as with the handle assembly 260, may be fast or course and/or slow or fine. During course movement the imaging system 20 may be moved rapidly, such as about 0.9 miles per hour (MPH) to about 2.0 MPH, including about 1.5 MPH based on a measured or sensed force applied by the user 69. During fine movement, the imaging system 20 may be moved more slowly, such as about 0.01 MPH to about 0.3 MPH, including about 0.15 MPH based on a measured or sensed force applied by the user 69. The imaging system 20 may be moved in at least three axes by driving the omni-directional wheels 144-150 according to an appropriate control scheme. Appropriate control schemes include those that drive one or more of the wheels 144-150 to move the imaging system 20 in a selected manner such as along a selected axis of motion and in multiple axes of motion. Driving the wheels 144-150 may also be done in a closed or open loop with or without feedback form the wheels.

Driving the omni-directional wheels at different speeds and/or directions may cause different total movement of the imaging system 20. Accordingly, the imaging system 20 may be moved in a first axis 274. The first axis 274 may be an axis that is generally along a long axis of the subject, such as the patient 40. Additionally, the motion controller 268 may operate the motors 178-192 to move the imaging assembly 20 in a second axis 276, which may be substantially perpendicular to the first axis 274. The two axes 274, 276 may allow movement of the imaging system 20 generally in a plane.

The movement plane defined by the axes 274, 276 may be substantially parallel or defined by a surface 280 on which the imaging system 20 is placed. Further the imaging system 20 may rotate around an axis 282, which may be substantially perpendicular to the first axis 274 and the second axis 276. Generally the imaging system 20 may rotate in the direction of arrow 284 around the axis 282. Further the imaging system 20 including the gantry 48 may move in the direction of the axis 282 which is substantially perpendicular to the axes 274, 276. Further, the gantry 48 may move in the direction of axis 282 and this movement may not be movement due to the drive assembly 140, although the motion controller 268 may be used to move the gantry 48 also in the direction of the axis 282.

Accordingly, the handle assembly 260 may be used to move the imaging system 20. Movement of the imaging system 20 may be performed during operation of the imaging system 20, such as gathering image data of the patient 40. The handle assembly 260 may also be used to move the imaging system 20 to a selected location relative to the patient 40 and then released while gathering image data of the patient 40. Therefore, it is understood that the handle assembly 260 may be used to move the imaging system 20 at any appropriate time such as prior to, during, or after imaging a patient 40.

It is further understood that handle assemblies may be positioned at other locations on the imaging system 20. For example, a second handle assembly 290 may be positioned away from the handle assembly 260. The second handle assembly 290 may also include a handle 292 and a sensor assembly 294. The sensor assembly 294 may be similar to the sensor assembly 264 and be in communication with the motion control 268. The handle assembly 290 may move the imaging system 20 in all of the directions or along the axes 274, 276, 282, and 284, as discussed above or a limited number thereof. For example, the second handle assembly 290 may be used to move the imaging system 20 from a first gross location (e.g. a storage locker) to a second gross location (e.g. an operating room). Therefore, the second handle assembly 290 may be limited in movement of the imaging system 20 generally along the axes 274, 276 and in the direction of arrow 284.

Figure 4B:
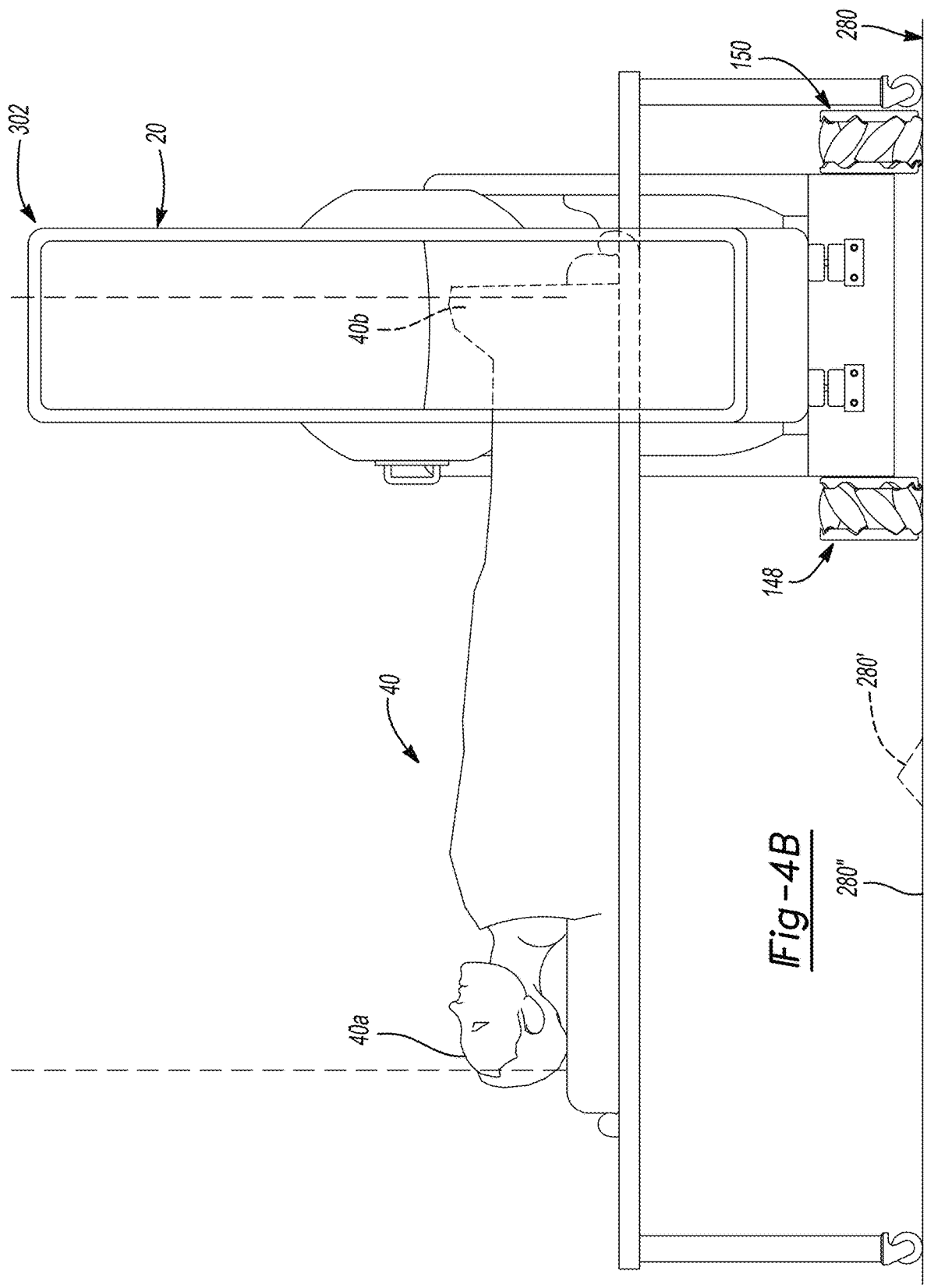
FIG. 4B is a schematic view of the imaging system in a second position.

Moreover imaging of the patient 40 may be done substantially automatically, manually, or a combination of both. With continuing reference to FIGS. 1-3 and additional reference to FIGS. 4A and 4B, the imaging system 20 is movable relative to the patient 40. As illustrated in FIGS. 4A and 4B the patient 40 is positioned on the support 120, such as a hospital bed or operating room (e.g. radiolucent) bed. It is understood that patient 40 may be positioned at any appropriate location or room. Nevertheless, the imaging system 20 may move relative to the patient 40 to acquire image data for generation of the image 114 to be displayed on the display device 64, or any other appropriate display device.

As illustrated in FIG. 4A, the imaging system 20 may be positioned at an initial or starting position or location 300 relative to the patient 40. During operation and movement of the imaging system 20, the patient 40 need not move, according to various embodiments. The imaging system 20 may be moved relative to the subject in any appropriate manner or direction, or combination of direction to movements including those discussed above. For example, the imaging system 20 may move along axis 274 in the direction of arrow 274', as illustrated in FIG. 4A. Accordingly, the imaging system 20 may move from near a head 40a of the patient 40 towards a foot 40b of the patient 40, as illustrated in FIG. 4B.

During movement of the imaging system 20 the gantry 48 may move in the direction of arrow 274' and/or the entire imaging system assembly may move in the direction of arrow 274'. During movement of the entire imaging system 20, including the gantry 48 and the cart 100, the motion controller 268 may operate the drive assembly 140, including the omni-directional wheels 148, 150 to move the imaging system 20 generally in the direction of arrow 274'. The imaging system 20 may include various portions, such as those discussed above, which may also rotate around a patient 40, such as around a long axis of the patient.

As the imaging system 20 moves in the direction of arrow 274', including the cart 100, the omni-directional wheels of the drive system 140 may rotate to move the imaging system 20 in the direction of arrow 274'. The imaging system 220 moves along the surface 280, which may also support the patient support 120. It is understood that the surface 280 may be substantially smooth and planer for movement of the imaging system 20. It is further understood, however, that surface 280 may include imperfections, such as bumps or projections 280' that extend above a lower or flat portion 280" of the surface 280. Similar low spots or depressions (not illustrated) may be present).

During movement of the imaging system 20 from the starting position 300, illustrated in FIG. 4A, to an ending or a second position 302, illustrated in FIG. 4B, the imaging system 20 may encounter the bump 280'. The bump 280' may move one or more of the omni-directional wheels 144-150 generally in a direction away from the flat surface portion 280", such as in the direction of arrow 304. During movement of the selected omni-directional wheel, such as the omni-directional wheel 150, the orientation or position of various portions of the imaging system, such as the detector 54 may move relative to the patient 40 from an intended path, such as one generally along a plane and defined by the axes 274, 276. The resultant image data may, therefore, not be aligned with all image frames or acquisitions of the image data acquired with the imaging system 20.

The imaging system 20 may include additional sensors such as those included in a position measurement sensor, which may be referred to as an inertial measurement unit (IMU) 310. The IMU 310 may include one or more accelerometers and one or more gyroscopes. The IMU 310 may be incorporated into various portions of the imaging system 20, such as the detector 54, the gantry 48, the imaging system support base 103 of the cart 100, or other appropriate locations.

The IMU 310 may determine an amount of movement of the respective portions such as the detector 54 during movement of the imaging system 20 and or a total motion of the imaging system 20 during movement of the imaging system 20. The determined motion of the imaging system 20, such as the detector 54 or including only the detector 54, may be incorporated into a reconstruction of the image 114 from the image data. For example, a movement of the detector 54 in the direction of arrow 304 of about 1 mm may be determined during acquisition of the image data. The image data acquired during the displacement of the detector 54 may be aligned with the remaining image data based on the measured or determined amount to create a substantially error free or clear image data 144.

In various embodiments, the IMU 310 may transmit a sensed movement, including a magnitude of movement and a time of movement to the image processing unit 102, or other appropriate processing unit. The appropriate processing unit, such as the imaging processing unit 102, may incorporate the amount of movement and time of movement to align all of the image data acquired of the patient 40.

The IMU 310 may include three accelerometers and three gyroscopes and, therefore, may provide 6 degrees for sensing freedom of movement of the imaging system 20 and/or portions thereof. The IMU 310 may sense the deviations and make a correction to the imaging data in an open loop fashion. In other words, the time and amount of movement may be determined and incorporated into image data acquisition and/or image reconstruction by the imaging processor 102 and/or the navigation processor 110 In various embodiments, the IMU 310 may also or alternatively be operable in a closed looped manner around the IMU 310 to make selected axes of the gantry 44 and/or the imaging system 20 as a whole inertially stable (X, Y, Z, Tilt, wag). In other words, the imaging system 20 as a whole or the gantry 44 and/or the imaging portion 46 may be moved to ensure that the image data is collected in an inertially stabile manner. That is the various portions of the imaging system 20 may be moved based upon a signal from the IMU 310 to compensate for sensed and/or determined movement. Generally, an axis of rotation of the rotor 56 will not be inertially stabilized since it may rotated 360 degrees around the patient 40 for imaging purposes.

Further, the IMU 310 may be used for navigation. The information from the IMU 310 may be used by the drive controller 268 to insure the imaging system 20 maintains a course in inertial space during image data acquisition. In various embodiments, more than one of the IMU 310 may be present. Because the drive control 268 and the drive system 140, 340 may use three axes of motion, the IMU for the drive may include only two accelerometers (x/y direction) and one gyroscope for rotation about the vertical axis. This would be used to insure it drives along the table 120 and the patient 40 in a selected manner, such as a straight line, a spline move, or with multipoint guidance. The use of an IMU 310 in either case is optional, however.

In addition to the IMU 310, or alternatively thereto, the tracking system 30 may also be used to determine movement of the imaging system 20. As discussed above, the imaging tracking device 72 may be positioned on the imaging system 20. During movement of the imaging system 20 in the direction of arrow 274' the tracking system may track movement of the imaging system 20, including the gantry 48. The tracked location of the imaging system 20 during acquisition of the image data may also be used to ensure alignment of the image data along a selected axis, such as the axis 274. Thus, the tracking system 30 may be used to generate or provide position data regarding the location of the imaging system 20 over time, such as while acquiring the image data.

Figure 5:
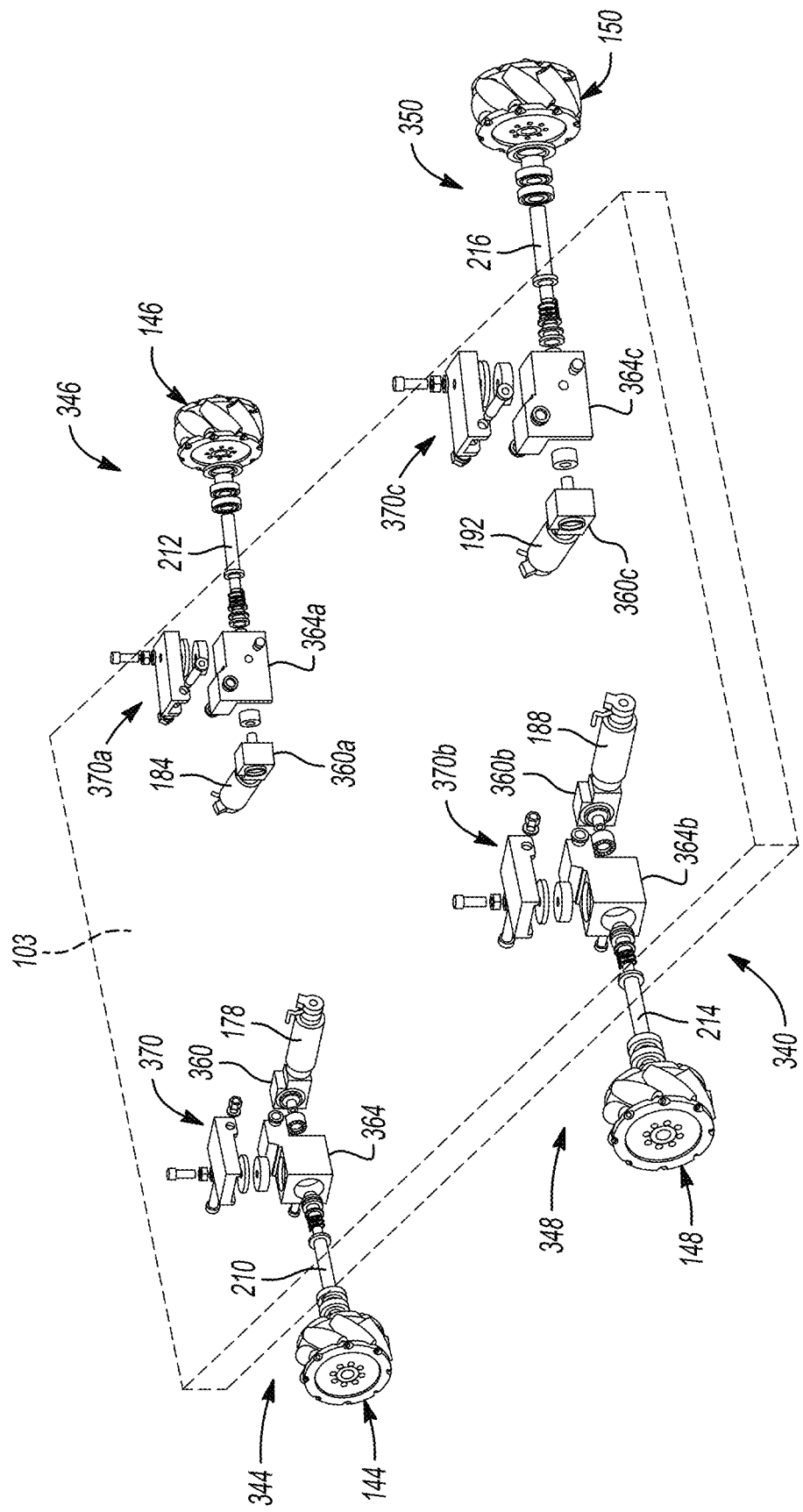
FIG. 5 is a perspective view of a drive system.
Figure 6:
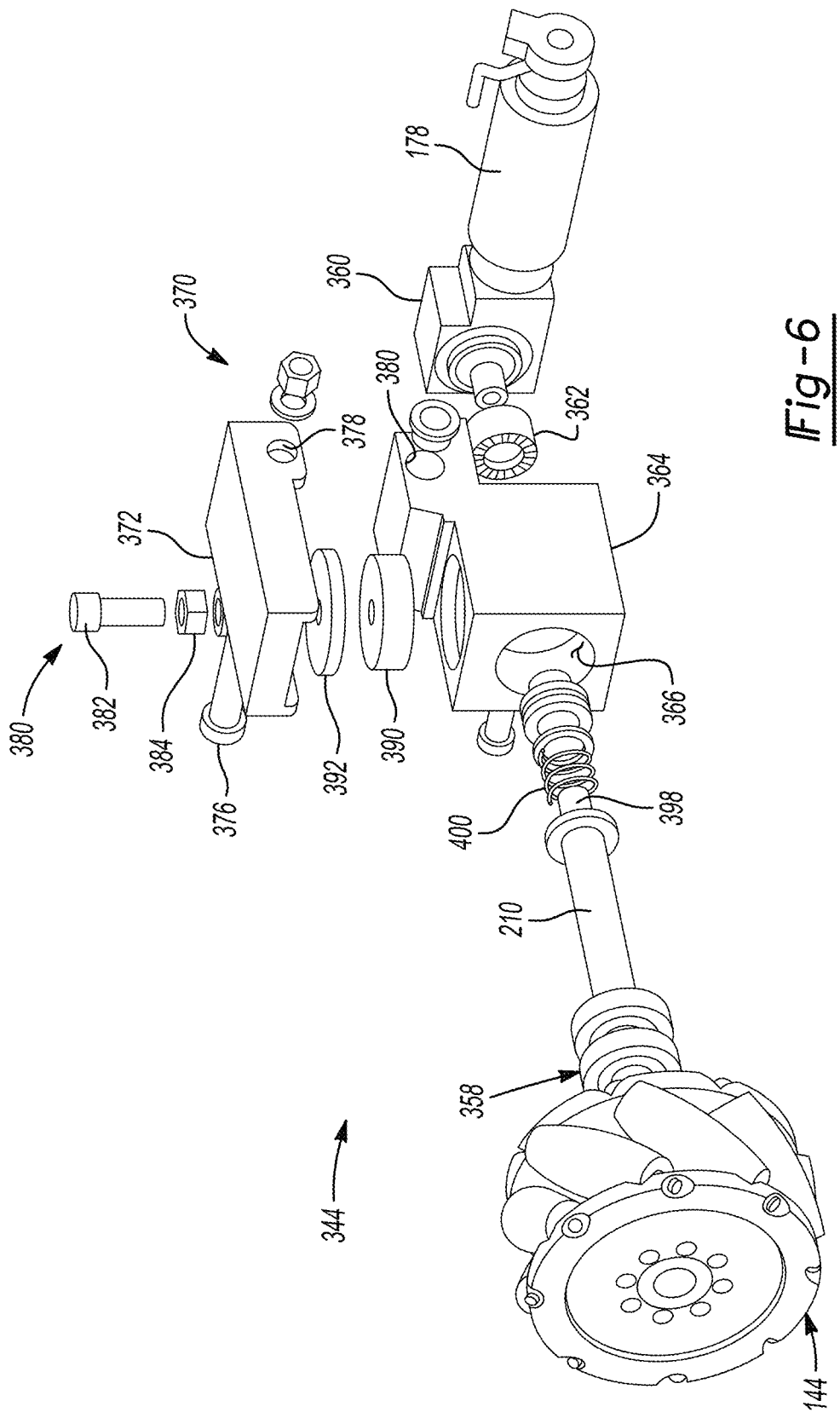
FIG. 6 is a first perspective detail view of a drive sub-assembly of the drive system illustrated in FIG. 5.
Figure 7:
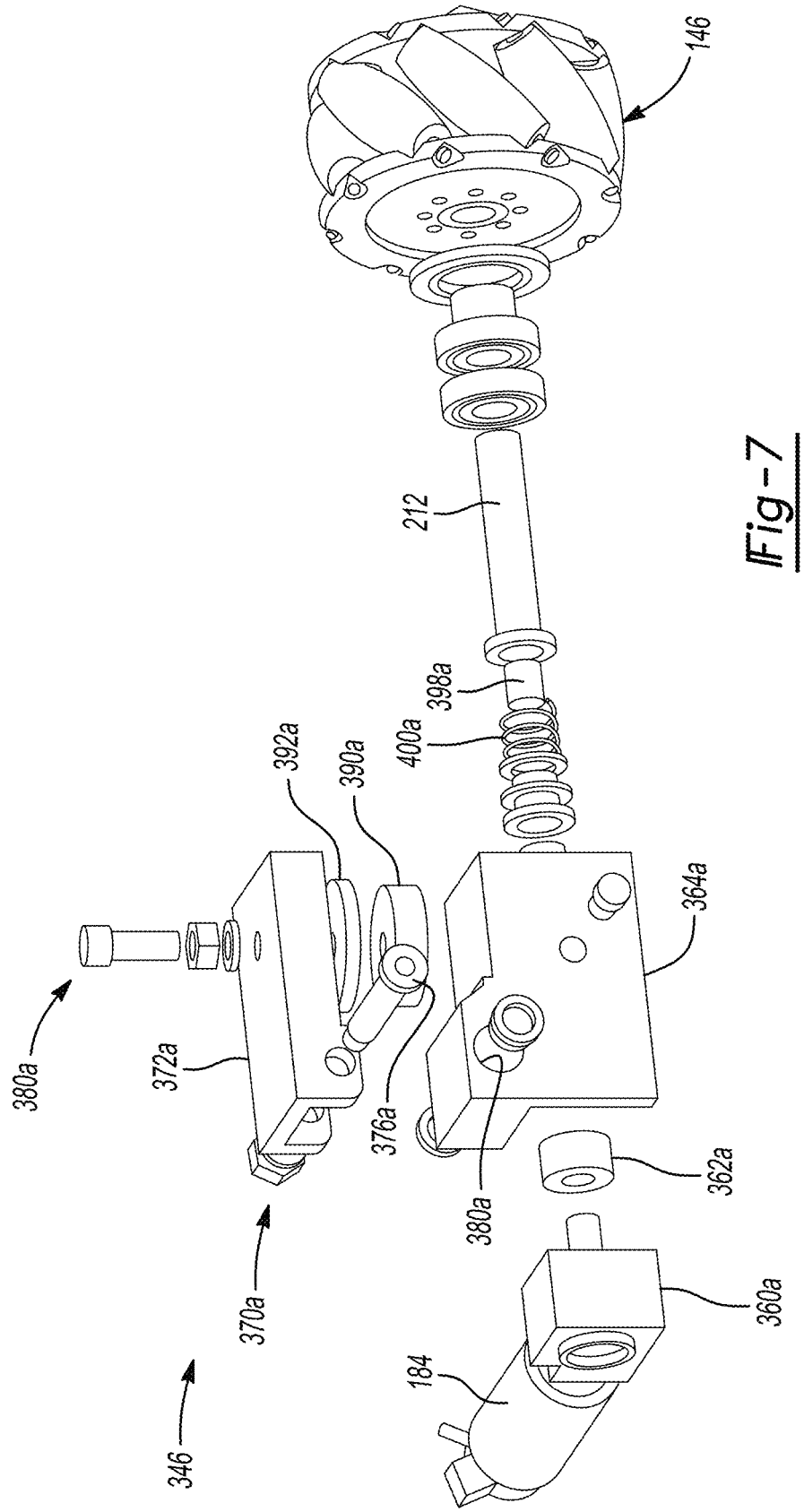
FIG. 7 is a second perspective detail view of a drive sub-assembly of the drive system illustrated in FIG. 5.

As discussed above, in relation to FIG. 1, FIG. 2, and FIG. 3, the imaging system 20 may include or incorporate a drive system 140. The drive system 140 may include one or more supports, such as wheel supports, which may include omni-directional wheels. The omni-directional wheels 144-150 may be connected to and/or incorporated into selected structures, such as the frame structures of 198,200. It is understood, however, that the supports, such as the wheels 144-150, need not be incorporated into the frames 198,200 discussed above. Turning reference to FIG. 5, FIG. 6, and FIG. 7, the imaging system 20 may incorporate a drive assembly 340. The drive assembly 340 may include selected sub-assemblies, such as independent drive sub-assemblies. The drive assembly 340 may include a first independent drive sub-assembly 344, a second independent drive sub-assembly 346, a third independent drive sub-assembly 348, and a fourth independent drive sub-assembly 350. Each of the drive sub-assemblies 344-350 may include various components, such as those illustrated specifically in FIGS. 6 and 7. The drive sub-assemblies 344-350 of the drive assembly 340 are mounted or connected to the imaging system 20, such as to the base or support portion 103. As illustrated in FIG. 5, the support base 103 is connected to each of the independent drive sub-assemblies 344-350. It is understood that the imaging system 20, including the portions discussed above, may otherwise be associated with the support base 103. Illustration of only the support base 103 is simply for the present discussion. It is further understood that the imaging system 20 may include all of the features discussed above and the possible movements, as discussed above due to the drive assembly 340.

Each of the drive sub-assemblies 344-350 may be associated with supports such as the wheels 144-150, as discussed above. The wheels 144-150, therefore, are not discussed again in detail, but may include features including those discussed above. In various embodiments, the drive sub-assembly 344 may include or be connected to the wheel 144. It is understood that each of the drive sub-assemblies may include similar components as the drive sub-assembly 344 and will not be discussed in detail independently. Similar components of the drive sub-assemblies 346-350 include similar reference numbers augmented with a lower case letter.

The wheel 144 of the drive sub-assembly 344 is connected a drive motor, such as the drive motor 178 through the axle 210. The assembly 344 may include one or more bearing and/or connection components 358. The drive motor 178 may be connected to the axle 210 by a geared reduction mechanism 360. The geared reduction mechanism 360 may reduce the motor an appropriate amount, such as about 50 to 1. Therefore, the motor 178 may drive the wheel 144 in appropriate manner and speed. Further, a drive connection member 362 may interconnect with the axle 210, as discussed herein.

The motor 178 may be mounted relative to the base 103, such as fixedly to the base 103. The drive motor 178 may interconnect with the wheel 144 through a connection or mounting block 364. The mounting block 364 may be positioned relative to the base 103 and allow for connection of the motor 178 to the wheel 144, such as through a passage or bore 366. The mounting block 364 may be movably connected to the base 103 through a pivot mechanism 370. The pivot mechanism 370 may include a rigid mounting block 372 that is rigidly or fixedly connected to the base 103. A pivot pin 376 may pass through a bore 378 of the block 372 and through a second bore 380 of the mounting block 364.

The drive assembly 344 further includes a mounting or pre-tensioning assembly 380. The pre-tensioning assembly 380 may include a bolt 382 and a nut 384 and various other components, or selective alternatives to these components. The pre-tensioning assembly 380 allows for tensioning of a damping or shock absorption.

The drive assembly 344 may include or allow for a shock absorption or damping of motion of the base 103 due to the floor 280 by allowing the mounting block 364 to pivot and move relative to the fixed block 372 due to the pivot mechanism 370. A shock absorbing or damping material or assembly, such as a first damping member 390 and a second damping member 392 may be provided between the mounting block 364 and the fixed block 372. It is understood that more or less of the damping members may be provided and the two are merely exemplary. Further, the materials may be selected to allow for a selected amount of shock absorption or damping of movement of the mounting block 364 relative to the fixed block 372 and may be similar to the mounts 250, discussed above. Accordingly, the wheel 144 may move relative to the base 103 during movement, as discussed above, of the imaging system 20 without substantially moving the imaging system 20. The damping assembly 390, 392 can absorb forces in a selected amount of movement of the wheel 144 relative to the base 103. Also, each of the sub-assemblies 344-350 may include separate ones of the damping portions. Thus, each of the wheels 144-150 may be moveable independently relative to the base 103 and allow for independent suspension of the wheels 144-150.

Further the drive assembly 344 may include a lock-out system wherein the axle 210 includes a spline 398 that disengages from the gear mechanism 360 under selected conditions. A spring member 400 may be used to bias or hold the axle 210 away from the gear mechanism 360 when the motor is not being powered or under selected conditions, such as high motor speed or imaging system speed. Accordingly, in an emergency or non-operative condition the wheel 144 would not be driven by the motor 178.

It is understood that the drive assembly 340 may include a selected number of drive sub-assemblies, such as the four drive sub-assemblies 344, 348, 346, 350. It is understood that any appropriate number of drive sub-systems may be provided and four is merely exemplary, for example three or five may be provided. Nevertheless, each of the drive sub-assemblies 344-350 may include substantially similar or identical components, which are not repeated here. Each of the drive sub-assemblies 344-350, or the wheels as discussed above, may be operated substantially and/or completely independently of each other. In other words, each of the wheels may be operated at different speeds or directions. Components that are the same are given like reference numerals augmented with a lower case letter.

Further, it is understood that the drive assembly according various embodiments, including the drive assembly 140 and/or the drive assembly 340, may be included with other types of wheels or omnidirectional wheels, such as those discussed above. The types of wheels may include mecanum wheels and/or Rotacaster® omnidirectional wheels sold by Rotacaster Wheel Limited having a place of business in Tighes Hill, Australia.

Further, it is understood that an appropriate selected number of wheels, according to various embodiments, may be provided relative to the imaging system 20. For example, three wheels may be positioned substantially 120 degrees to one another to move the imaging system 20 in the selected axes, as discussed above. Further, it is understood that four or five wheels may also be positioned relative to the imaging system 20 to move the imaging system 20 in a selected manner. It is also understood that the imaging system 20 may be driven in various directions by driving selected wheel(s) in an appropriate manner. For example, two wheels may be positioned opposite one another as a pair a second pair of wheels may be positioned opposite one another. Each of the wheels may be placed on axles that extend along axes such that each pair of wheels extends along the same axis that is perpendicular to the axis of the other wheels. Operation of the wheels, therefore, may move the imaging system in a first or perpendicular axis, rotation around an axis, or diagonal relative to an origin defined by the two pairs of wheels.

Figure 8:
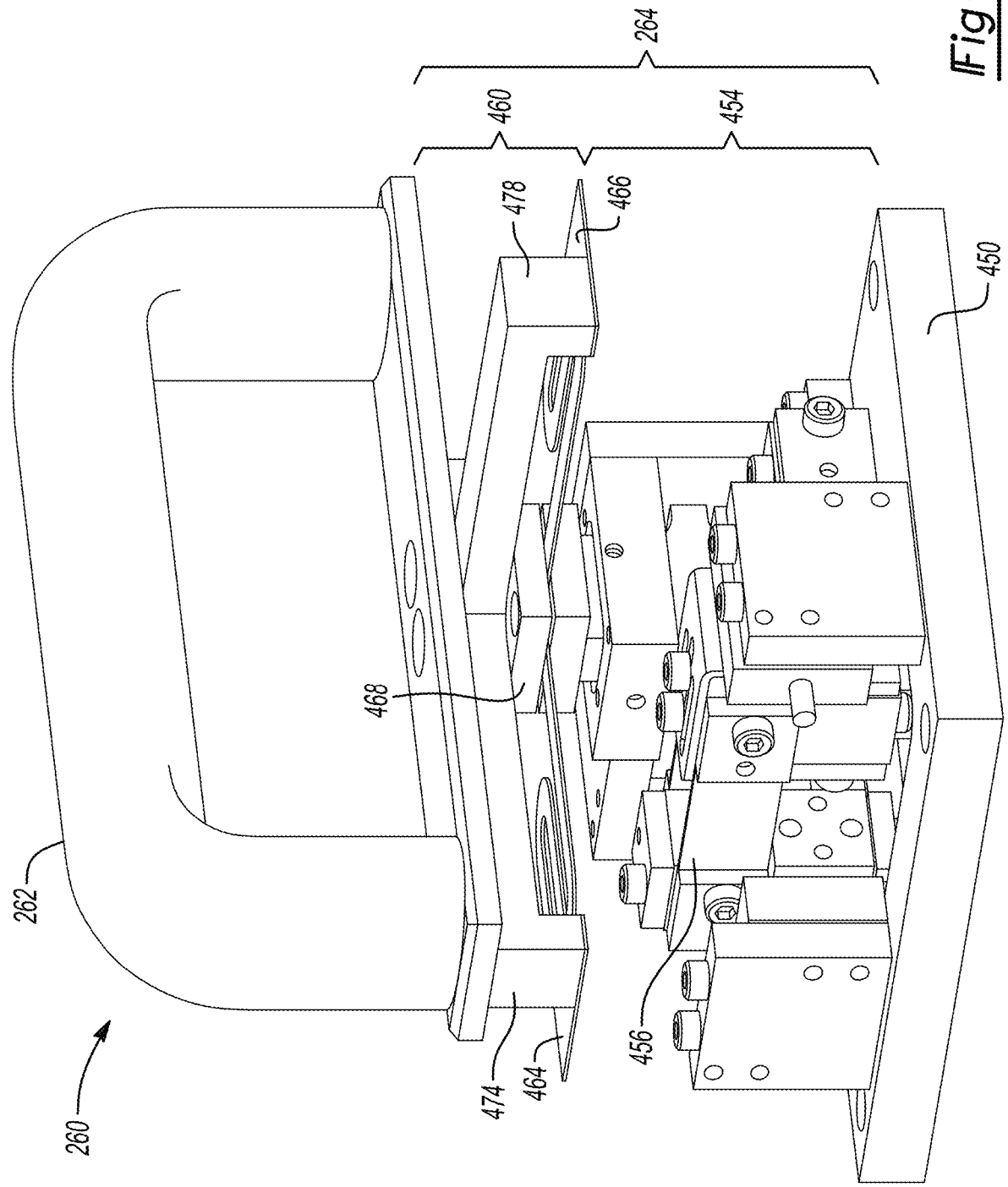
FIG. 8 is a detail view of a handle assembly, according to various embodiments.

Returning reference to FIG. 1 and with additional reference to FIG. 8, the handle assembly 260 is illustrated in greater detail. As discussed above, the handle assembly 260 includes a graspable member or handle 262. The handle 262 includes a dimension that allows it to be grasped by a user, such as the user 69 to move the imaging system 20 in a selected manner, such as in 5 degrees of freedom. The handle assembly 260 may be moved to actuate or move only the gantry assembly 44 relative to the cart 100 in a rapid manner. Further, in various embodiments, the handle assembly 260 may also move the cart 100 to move the entire imaging assembly 20. Thus, the handle assembly may move only the gantry 44, only the entire imaging system 20, or both the gantry 44 separate from the entire imaging system 20.

The sensor assembly 264 may include various sensor portions that are mounted to a ridged base 450 that is rigidly connected to at least a portion of the imaging system 20, including the cart 100, the gantry 48, or other appropriate portions. The sensors may include flexures, pressure sensors, tensions sensors, positions sensors (e.g. joystick), etc. The sensor assembly 264 then includes various portions such as a first sensor sub-assembly 454 that may operate or move the gantry 44 in selected axes, such as a X-axis, Y-axis, or Z-axis relative to the subject 40. In various embodiments, the axes may be substantially defined by the axes 274, 276, 282, as discussed above. For example, X axis may generally be along the axis 46a of the patient 40.

The first sensor sub-assembly 454 may be similar to that included in the O-Arm® imaging systems sold by Medtronic, Inc. having a place of business in Minneapolis, Minnesota. The first sensor sub-assembly 454 may include one or more flexure sensors, such as the flexure sensor 456. Movement of the handle 262 relative to the ridged base 450 causes a force applied to the flexure 456. The force applied to the flexure 456 may be sensed and a signal generated to cause a selected movement of the gantry 44 and/or the entire imaging system 100, such as controlled by the motion controller 268. The signal may be generated based upon a pressure or movement of one end or portion of the flexure relative to another portion. The signal may be based on a distortion of a live wave, resistance, etc.

A second sensor sub-assembly 460 may include a second flexure 464 and a third flexure 466. It is understood that any appropriate number of flexures may be included in the sensory assembly 264 to sense movement of the handle 262 relative to the base 450. Further, it is understood, that the sensors may be any appropriate sensors and need not be flexures. Nevertheless, in various embodiments the flexures 464, 466 extend between a central base or connection 468 and respective arms or projections 474, 478 connect to second ends of the respective flexures 464, 466. Movement of the handle 262, which is connected to the arms 474, 478 cause flexion of the flexures 464, 466. Flexion of the flexures 464, 466 is sensed and a signal may be generated to cause movement of the gantry 44. In various embodiments, the flexures 464, 466 may operate to cause tilt and/or wag of the gantry 44. Wag may be rotation of the gantry 44 generally in the direction of double headed arrow 284. Tilt may be tilting the gantry 44 such that the plain of the gantry is moved to a non-perpendicular angle relative to the axis 46a of the patient 40. Accordingly, the respective flexures 464, 466 may generate signals either alone or in combination to cause tilt and wag of the gantry 44.

The handle assembly 260 may be operated to move the gantry 44 in a rapid or quick manner. This may allow for positioning of the gantry 44 relative to the subject 40 for imaging of the subject 40, as discussed above. Further the handle assembly 260 may be used to move the imaging system 20 by controlling the drive assembly, such that the drive assembly 140, 340 to move the imaging system 20 including the cart 100. Accordingly, it is understood that the handle assembly 260 may be used to move the gantry 44 alone or in combination with the cart 100, and also to move the cart 100 alone or in combination with the gantry 44.

Figure 9:
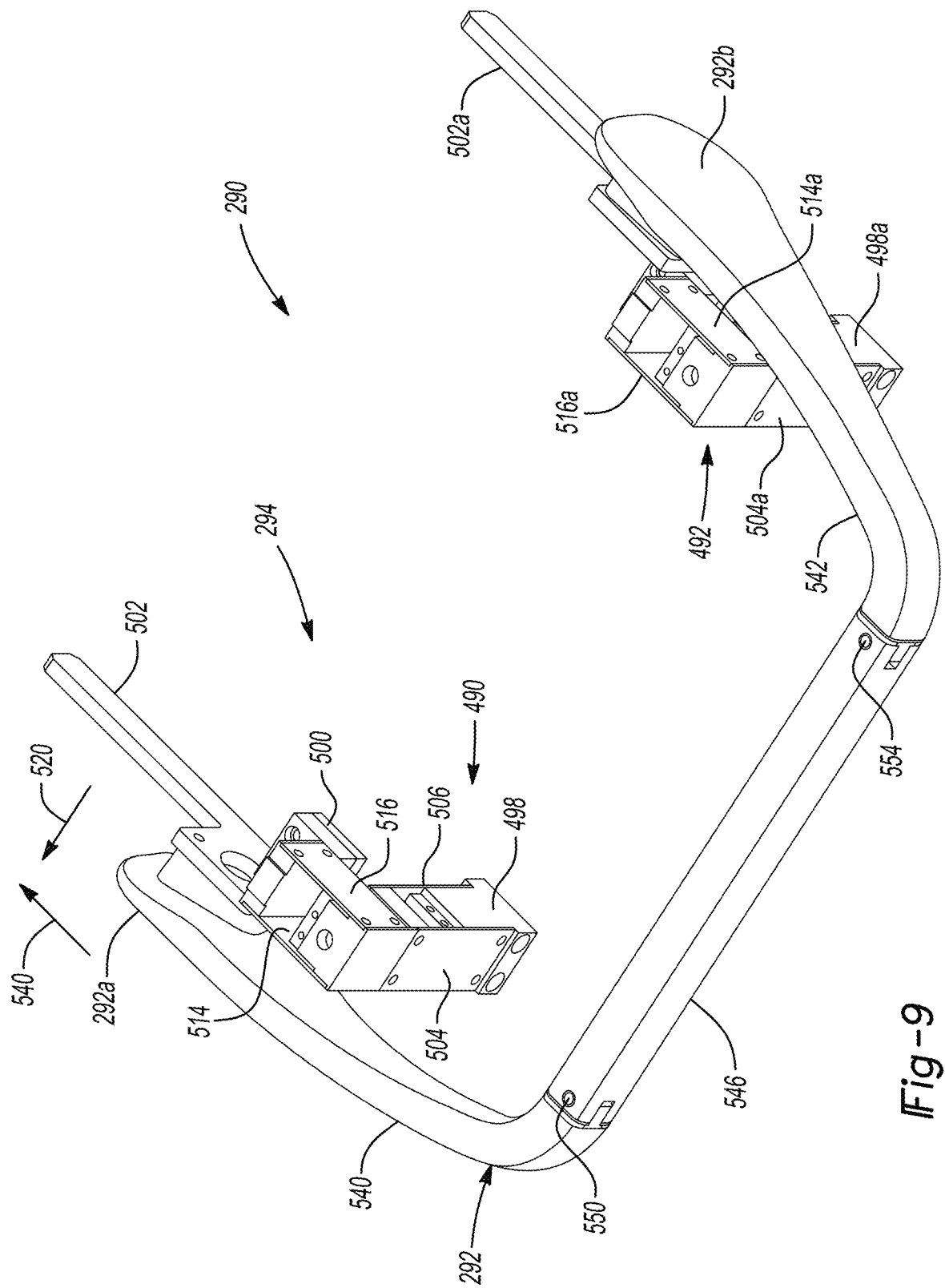
FIG. 9 is a detail view of a handle assembly, according to various embodiments.

With continuing reference to FIG. 1 and additional reference to FIG. 9 the second handle assembly 290 is illustrated and discussed in greater detail. The handle assembly 290, as discussed above includes the handle assembly 292 and sensor assembly 294. The sensor assembly 294 may include two sensor assemblies 490 and 492. The two sensor assemblies may be positioned at opposite ends or opposed ends of the handle 292 to sense forces or movement at the respective ends 292a and 292b of the handle 292. Each of these sensor assemblies 490, 492 may be substantially identical, and therefore items will not be repeated, but reference numerals for similar portions are included in the figures augmented by a lowercase letter.

The sensor sub-assembly 490 includes a base 498 that may be rigidly attached to the cart 100. The sensor sub-assembly 490 may include a second base 500 that is also rigidly connected to a structure of the cart 100. A connection member 502 may extend and also connect to the cart 100 and allow for selected movement of the handle 292 to be sensed by the sensor sub-assembly 490. The sensor sub-assembly 490 includes at least a first flexure 504 and may include a second flexure 506 to sense motion generally in the direction of arrow 510, which may be generally in the direction towards the cart 100 such as by pushing on the handle 292. The sensor sub-assembly 490 may also include at least a third flexures 514 and may include a fourth flexure 516 to sense movement of the handle 292, such as laterally relative to the cart 100 generally in the direction of arrow 520. As noted above the second sensor sub-assembly 492 may include similar portions to sense like movement relative to the cart 100.

The sensor sub-assemblies 490, 492 may include or send differential signals to the motion control 268 to cause movement of the drive assemblies 140, 340. Accordingly, force or movement applied to the handle 292 may cause the sensor assembly 294 to send signals to the motion control 268 to drive the cart 100 and, therefore, the imaging system 20 via the drive assemblies 340, 140.

The handle 292 may include a selected number of members, such as a first member 540 that is connected to the first sensor sub-assembly 490 and a second handle member 542 that is connected to the second sensor sub-assembly 492. A third handle member 546 may be movably coupled to the handle members 540, 542 at respective ends or portions of the third handle portion 546. In various embodiments, the third handle portion 546 may be movably coupled to the first handle member 540 by a pin 550 to allow for a selected amount of movement of the third handle member 546 relative to the first handle member 540. A second pin 554 may be provided to connect the third handle member 546 to the second handle member 542 to also allow a selective amount of movement of the third handle member 546 relative to the second handle member 542. Accordingly, the handle assembly 292 may be provided in a plurality of members for connection to the sensor assembly 294. The movement of the third handle member 546 relative to the first and second handle members 540, 542 may allow for a decoupling of the sensor sub-assemblies 549, 542 relative to one another. Accordingly, appropriate or selected signals from the sensor sub-assemblies 490, 492 regarding a selected motion or desired or selected motion of the handle 292 relative to the cart 100 may be sensed inappropriate signals sent to the motion control 286 to move the cart 100.

The imaging system 20 may be moved according to various appropriate techniques. In moving the imaging system 20, image data may be acquired of the patient 40 for various purposes. Regarding imaging, the image data could be acquired for use as a 3D mode or a 2D mode. In the 2D mode images may be stitched together create a long 2D image of the patient 40. In 3D mode, an image may be recreated in 3D space. In either case, moving the imaging system 20 relative to the patient 40 may allow for a large field of view of the patient with the final image created with the acquired image data. Further, determining a position of the imaging system 20 during the image data acquisition may assist in assuring a clear and error free final image based r created on the image data.

As discussed above the imaging system may be moved substantially manually by the operator 64 engaging one or more of the handle systems, such as the first handle system 260, to move the imaging system 20. Alternatively, or in addition thereto, the user 69 may input a selected imaging analysis, such as a three-dimensional reconstruction, and the imaging processing unit 102 may execute instructions to determine an appropriate movement of the imaging system 20 from the first location 300 to the second location 302 to acquire image data to perform the appropriate or selected reconstruction. It is understood that the user 69 may also select imaging of a selected portion of the patient 40, rather than an entire three-dimensional reconstruction. Also the imaging system 20, including the image processing unit 102, may then determine a movement of the imaging system including a rotation of the detector 54 and/or the emitter 52, movement of the gantry 48, or movement of the imaging system 20 using the drive system 140. All motions of the imaging system 20 may be used to move the imaging system 20 relative to the patient 40 to acquire the image data. The movement of the imaging system 20, therefore, may be substantially automatic based upon (including only upon) the input by the user 69 of the type of image data to be acquired and/or a desired resultant image or reconstruction of an image based on the image data.

Further, a combination of manual movement and automatic movement may be performed. For example, the user 69 may move the imaging system to move to a selected location, such as near a thoracic region of the patient 40. The user 69 may then identify a selected number of images and spacing of images and/or image data. The imaging system 20, at this selected location and/or a limited image acquisition region or volume, may then move, such as only rotating the detector and/or emitter 54, 52 and/or moving the gantry 48. Accordingly, it is understood by one skilled in the art, that the imaging system 20 may be moved manually or automatically, or a combination thereof to acquire image data of the subject 40.

In various embodiments, the various handle assemblies, such as the handle assembly 260, may be used by the user 69 to grossly or coarsely move the imaging system 20. Gross movement may include moving the imaging system 20 into a selected operating theater or near the patient 40. Fine movement may follow the gross movement, such as to acquire the image data. The fine movement may be substantially automatic, such as being driven by the imaging system controller 102 and/or the motion controller 268. Accordingly, the imaging system 20 may be moved relative to the subject 40 with the drive system 140 to acquire image data in either or both of a gross or course manner and/or a fine manner.

As discussed above, the imaging system 20 may include an appropriate drive system to assist in moving at the imaging system 20 from location to location, such as relative to the subject 40 and/or into an operating room or moving the imaging system from one operating room or location to another operating room. Further, the drive system may assist in moving the imaging system 20 for access to the subject 40 by the user 69 during a selected procedure, such as following or prior to imaging of the subject 40. The drive system may be oriented relative to the imaging system 20, such as the cart 100, the gantry 48, or other portions of the imaging system 20 to assist in moving the imaging system 20 and/or allowing access to the subject 40.

According to various embodiments, therefore, the imaging system 20 may include various drive systems, such as those discussed above and further herein. Within initial reference to FIG. 10 and FIG. 11, a drive system 640 may be incorporated or attached to the cart 100 of the imaging system 20. The drive system 640 may be similar to the drive system 340 illustrated in FIG. 5 discussed above.

The drive system 640 includes a plurality of multi-directional or omni-directional wheels, such as wheels similar or identical to mecanum wheels including a first hub member 644 and the second hub member 648 with one or a plurality of rollers 652 rotatably mounted between the hubs 644, 648. The roller 652 may be rotatably fixed to the hubs 644, 648 via axles 654 through the roller 642. The roller 652 may be rotatably positioned or mounted to the axle 654 while the axle is mounted to the hubs 644, 648 in a fixed manner. Alternatively thereto, however, the roller 652 may be fixed to the axle 654 and the axle 654 may rotate relative to the hubs 644, 648. It is understood, however, that the roller 652 may rotate independently relative to each of the other rollers on the wheel 642. The roller 652 generally rotates on a roller axis 664 relative to the hubs 644, 648 and an axis of the wheel, as discussed herein.

It is further understood that a selected number of wheels, such as four wheels designated herein as 642a, 642b, 642c, and 642d. Each of the wheels may be substantially identical to one another, save for their position relative to the base 103 of the cart 100. Further, the gantry 48 is not illustrated relative to the cart 100 in FIG. 10 and FIG. 11, but a gantry mount 48m is illustrated for reference. The gantry 48 may be mounted and moveable relative to the base 103 and due to the drive system 640.

Figure 10:
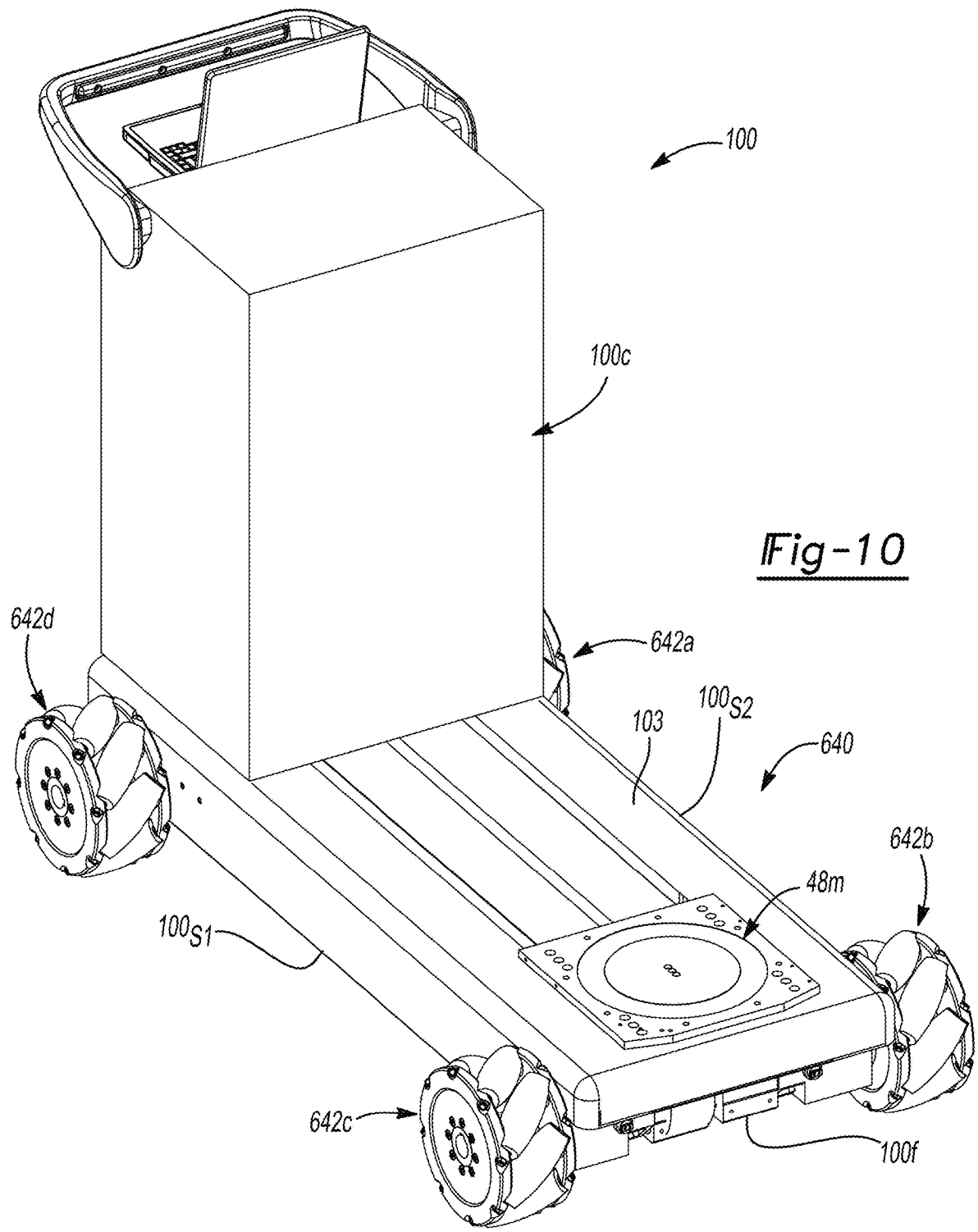
FIG. 10 is a top perspective view of an imaging system cart, according to various embodiments.
Figure 11:
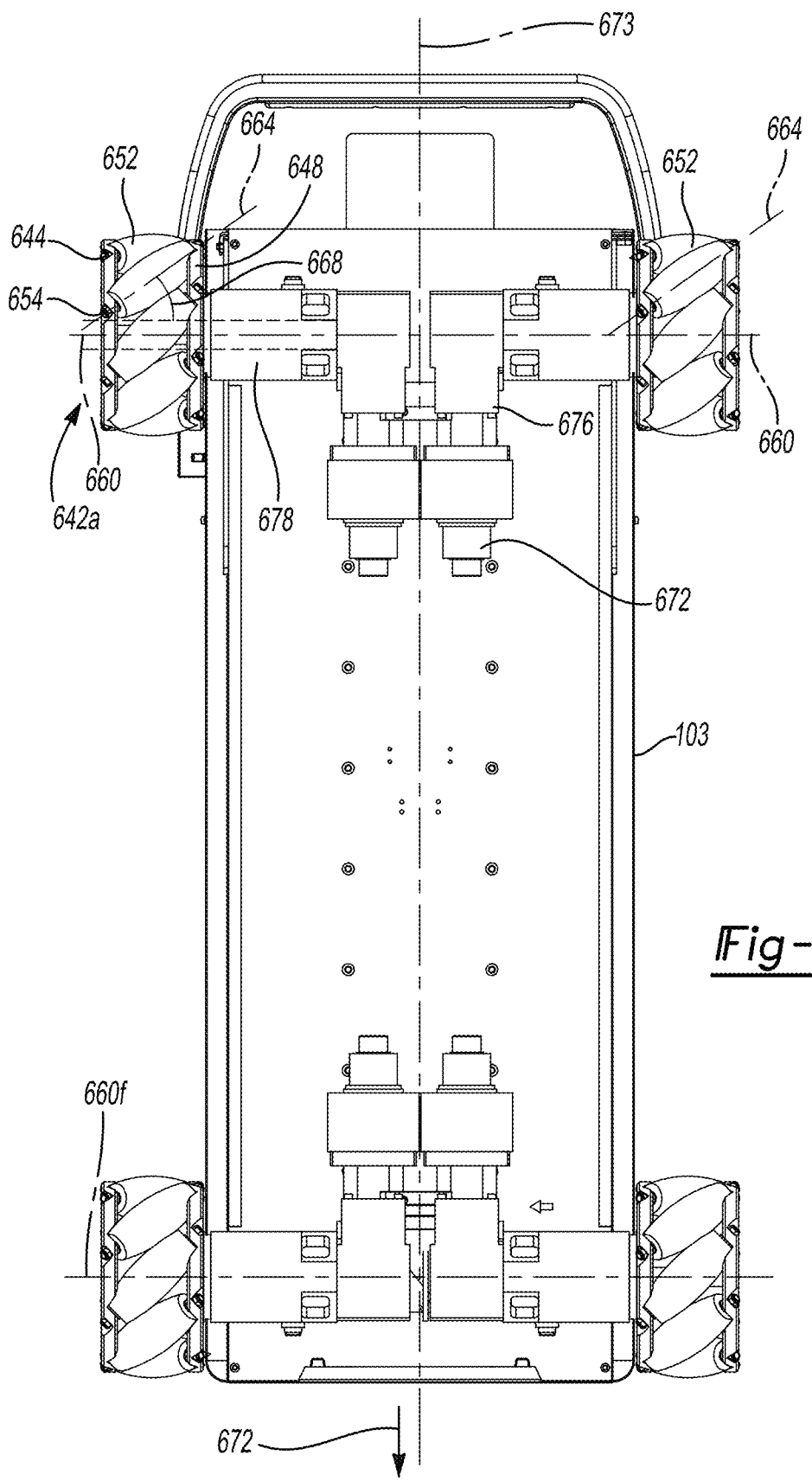
FIG. 11 is a bottom plan view of the cart of FIG. 10.

The base 103 may extend from a power and control portion 100c (i.e. near a rear of the cart 100) of the cart 100 toward a front 100f of the cart 100. The base 103 may also extend between a first side 100s1 and a second side 100s2. In various embodiments, as illustrated in FIG. 10 and FIG. 11, the base 103 may be substantially rectangular. Each of the wheels 642 may be positioned at or near a corner of the base 103. Generally, one of the hubs, such as the hub 648, may be positioned nearer the base 103 than the second hub 644. In various embodiments, the clearance between the hub 648 and the sidewall of the base may be only enough to allow for free-rotation of the wheel 642, but it is understood that the additional spacing may be provided.

Further, the hubs 644, 648 generally rotate around a wheel axis 660. Generally, the wheels 642 on opposite sides of the cart rotate around substantially the same axis 660, thus there may be a rear axis 660r and a front axis 660f. The rollers 652 are positioned on the respective wheel 642, however, are generally positioned to rotate around an axis 664 that is at an angle 668 relative to the rotational axis 660 of the wheel 642. In various embodiments, the angle 668 may be about 10 degrees (°) to about 90 degrees, including about 35 degrees to about 55 degrees, and further including about 45 degrees. It Is understood, however, that the angle 668 of the rollers 652 relative to the wheel axis 660, may also exist if the rollers were mounted at a center of the roller relative to one or more of a hub that is closer to a center of the wheel assembly 642.

Accordingly, if the base 103 is generally moving in the direction of the arrow 672 along a long axis 670 of the cart 103 the rollers 652 will have a force angle that is not aligned or parallel with the direction of travel of the base 103. Accordingly, an inefficiency of driving at the cart 100 in any direction may be greater than only having a wheel that rotates generally in the direction of travel and around the axis 660.

Similar to the system illustrated above, the respective wheel 642 may be each individually powered, and therefore controlled, via independent or individual drive systems that include motors. Each of the individual drive systems may include a motor assembly 672 and a gearing, such as a gear reducing, assembly 676. The motor 672 may drive the gear reducing assembly 676 to drive or rotate an axle mounted within a mounting block 678. The mounting block 678 may capture an axle 682 within the mounting block 678. The axle 682 may allow the wheel 642 to rotate around the axis 660.

Figure 12:
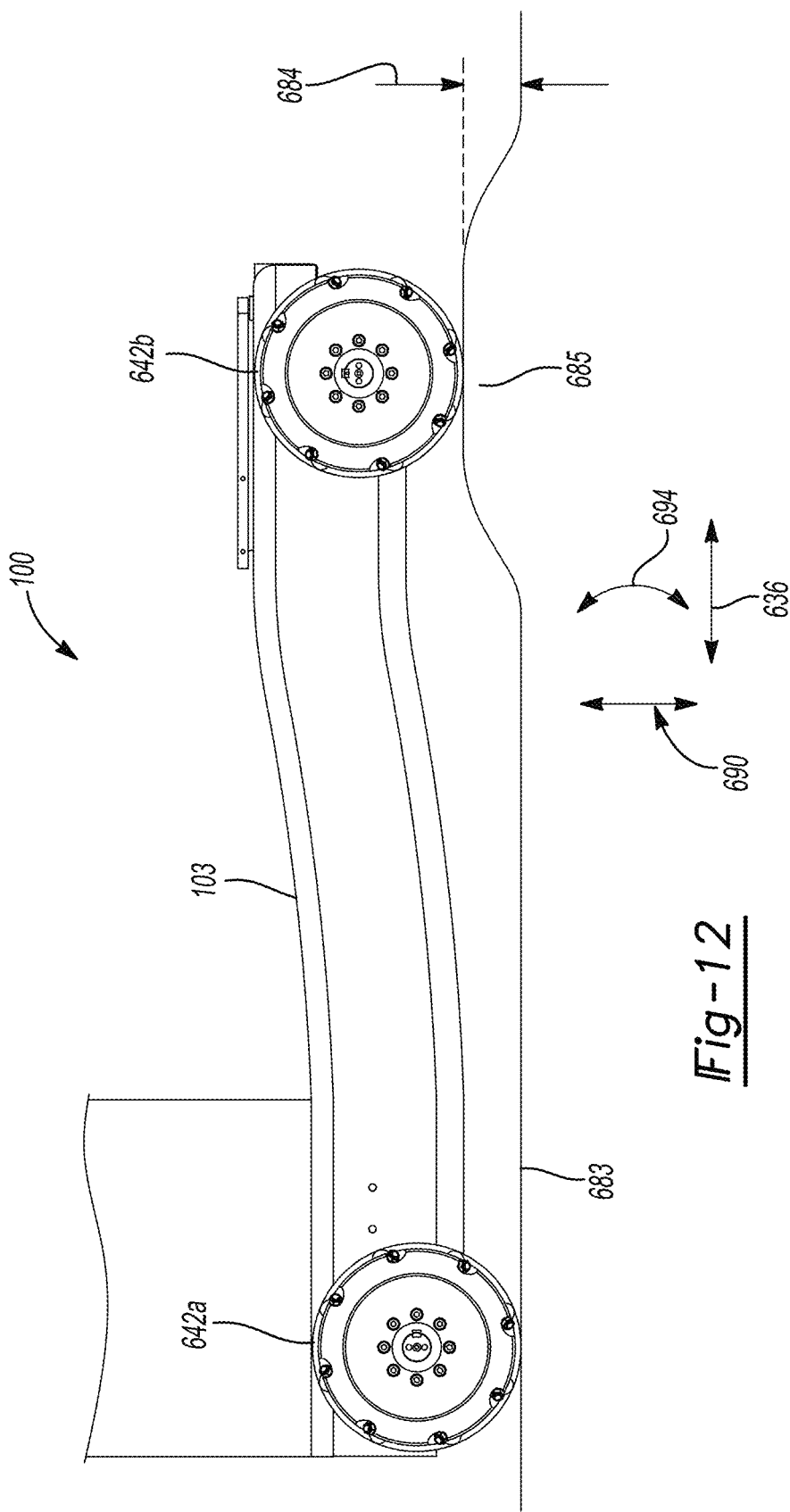
FIG. 12 is an environmental view of the cart of FIG. 10.

The mounting block 678 may be fixedly connected to the base 103. Accordingly each of the four wheels 642a-642d may have its respective mounting block 678 and axle 682 fixed relative to the base 103 at the respective corners, as illustrated in FIG. 10 and FIG. 11. The mounting block 678 may be generally rigidly fixed to the base 103. The cart 100, including the base 103, may, however, include a selected amount of flexibility. For example, when the wheels 642 are mounted to the base 103 and positioned on a flat surface, as illustrated in FIG. 12, the front wheel 642b may be raised or lowered a selected amount or distance 684, such as about 1 mm to about 5 cm, by a surface projection or depression 685. It is understood, however, that the base 103 may be formed with an appropriate flexibility to allow for movement of the cart 100 over a selected obstruction, such as an obstruction that would raise the wheel 642b about 1 mm to about 5 cm while maintaining all four of the wheels 642 in contact with the floor surface 683, including the surface projection or depression 685. Accordingly, the wheel 642, such as at the mounting block 678, may be rigidly fixed to the base 103 while still allowing for all four wheels to be maintained substantially in contact with the floor surface 683, even if an obstruction is encountered.

As discussed above, the respective axle 682 may be driven by the respective motor 672 to rotate the respective wheels 642. Upon driving the wheel 642, by powering the motor 672, the respective wheels will rotate based upon the input from the motor 672. The rotation around the axis 660 may generally be in a plane that is parallel with the sides 103s1, 103s2 of the base. The axis 660 is generally or substantially, such as within about 3 degrees of perpendicular to the long axis 673 of the cart 103.

Each of the four wheels may be powered substantially independently to move the cart 100 in any appropriate direction. For example, the wheel 642 may allow for movement of the cart 100 generally in the direction of double headed arrow 690, such as generally forward toward the forward portion 100f or rearward toward the control center portion 100c. Further, driving the wheel 642 in the respective manner allows for rotational movement, such as generally in the direction of curved double headed arrow 694 or in a lateral motion, such as generally in the direction of double headed arrow 696. The lateral motion in the direction of the double headed arrow 696 may be generally perpendicular to the double headed arrow 690. Therefore, according to various embodiments, the cart 100 may be moved in a direction that may be generally along the z-axis of the gantry 48, such as the axis 274 illustrated in FIG. 4A and discussed above.

The positioning of the four wheels 642 is generally at the corners of the base 103 and generally along the sides 103s1, 103s2 and allow for a substantial stability of the imaging system 100. As discussed above, the gantry 48 may move relative to the control portion 100c and relative to the base 103. As illustrated in FIG. 1, the gantry 48 may move generally along the directions of the various axes 274, 276, 282 and may also wag relative to the cart 100 such as generally along the curved line 284. Accordingly, positioning of the wheels 642 relative to the base 103 may allow for stability of the imaging system 20 during positioning of the gantry 48. Also, the center of gravity of the imaging system 20 may be substantially maintained within the four corners of the base 103 during any position of the gantry 48. Accordingly, the imaging system 20 with the wheels illustrated in FIG. 10 and FIG. 11, may be substantially stable even at a selected lean, such as on a ramp or angle of about 15 degrees or less, including about 10 degrees or less.

Therefore, during movement of the imaging system 20 including the wheels 642 substantially at the corners of the base 103, the imaging system 20 may remain substantially stable. Movement of the imaging system may require power to move the imaging system 20, such as by powering the motor 672. Powering the motor 672, however, would be required to overcome the forces of the rollers 652 mounted to the respective wheels 642 during movement along a surface, such as a floor. Accordingly, the drag or inefficiency relative to a single solid wheel rotating generally in the direction of the movement of the double headed arrow 690, may be about a cosine of the angle 668.

Figure 13:
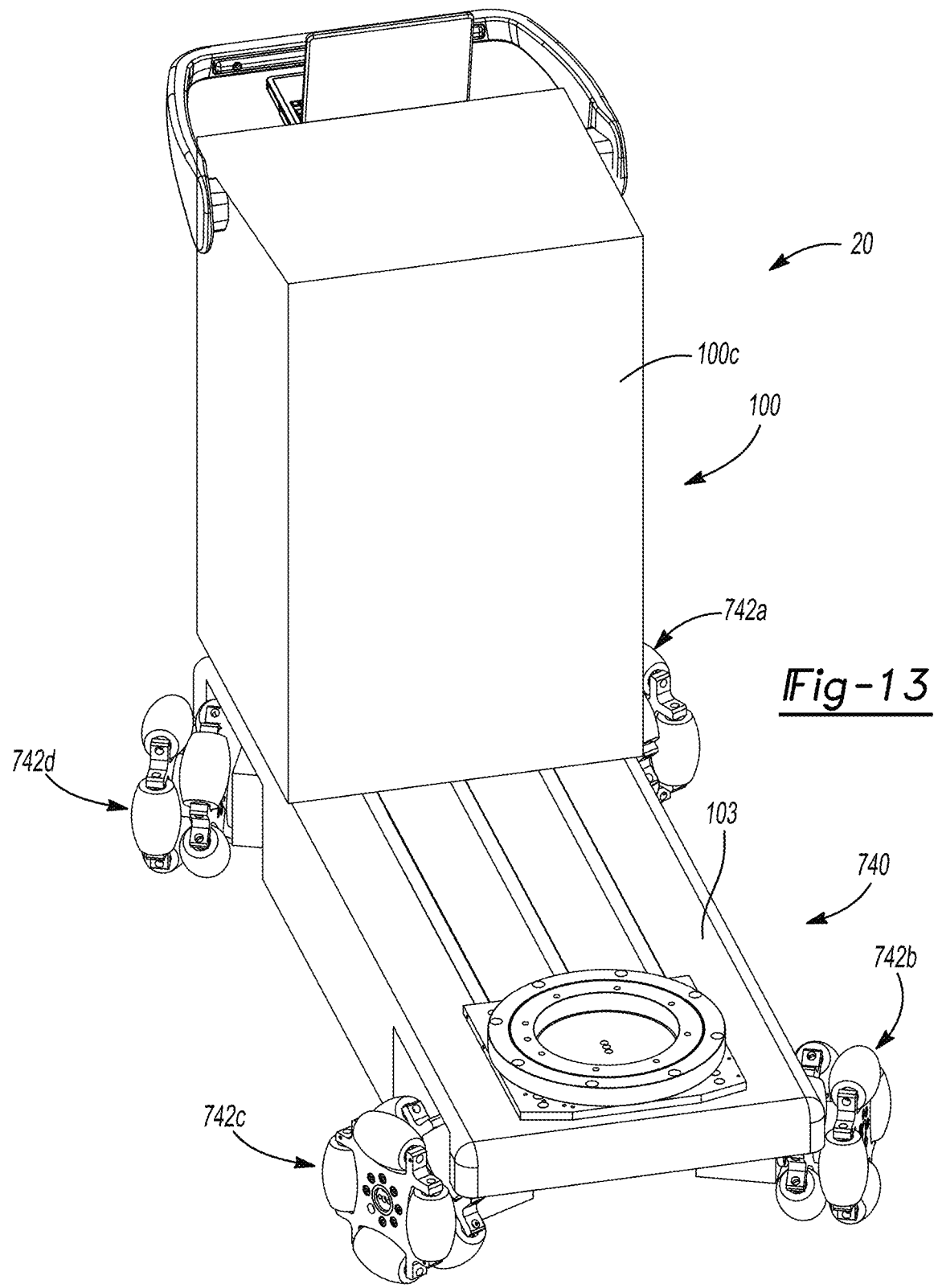
FIG. 13 is a top perspective view of a cart to hold an imaging system, according to various embodiments.
Figure 14:
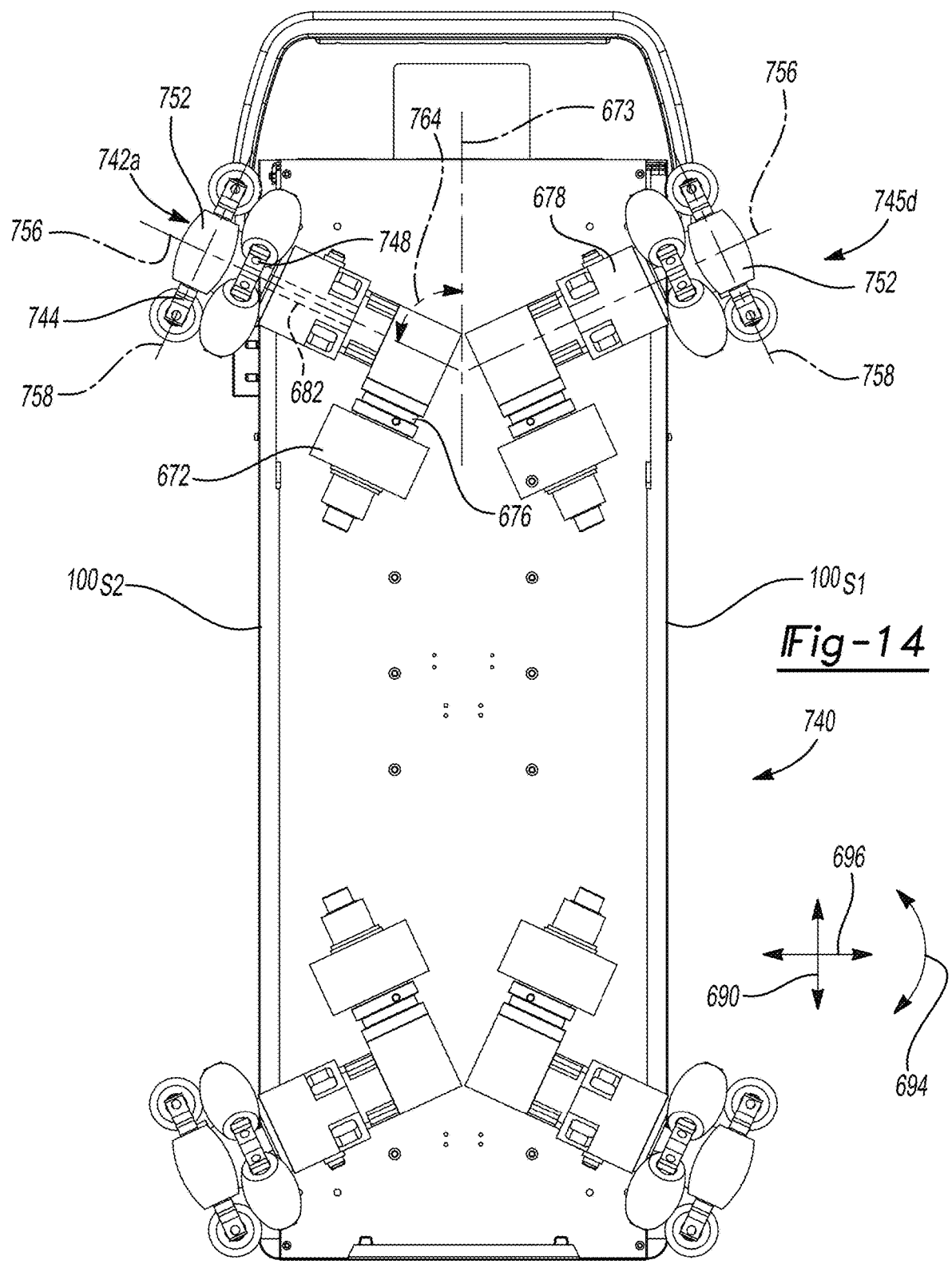
FIG. 14 is a bottom plan view of the cart of FIG. 13.

Turning reference to FIG. 13 and FIG. 14, a drive assembly 740 is illustrated. The drive assembly 740 may be mounted to the base 103 of the imaging system 20, similar to the drive system 640 discussed above and illustrated in FIG. 10 and FIG. 11. Further, the imaging system 20 is substantially identical to the imaging system 20, discussed above, including the cart 100 that will now be described in detail here. However, the drive system 740 may include a plurality of wheels 742, herein designated as four wheels 742a, 742b, 742c, and 742d. Each of the wheels 742 may include a first hub 744 and a second hub 748. The wheel 742, however, may differ from the wheel 642, by including a plurality of roller 752 that are generally mounted rotatably on the hubs 748, 744 respectively, rather than between the hubs 748, 744. As illustrated in FIG. 14, the wheel assemblies may include portions that are substantially similar to those discussed above, including the motor 672, the gearing or gear reducer 676, and mounting block 678. The wheel 742 may be rotatably mounted via the mounting block 678 by an axle 682.

With reference to FIG. 14, and with exemplary discussion of the wheel 742a, the wheel 742a may rotate on the axle 682 around an axis 756. The axis 756 which may be defined by the axle 682 and may be around which the respective hubs 744, 748 rotate. The roller 752 can only rotate around an axis 758 that is substantially perpendicular to the axis 756. Accordingly, the wheel 742a may generally move in the direction along the axis 756 without a contrary force vector relative thereto.

The base 103 may include the sides 100s1 and 100s2 and the long axis 673. The cart 100 may generally move in the direction of the double headed arrow 690, 694, and 696 as discussed above. The axis 756 of the axle 682 may generally be at an angle 764 relative to the axis 673 of the cart 103.

Each of the independent wheel assemblies 742 may have the respective axes 756 at the angle 764 relative to the central axis 696. As illustrated in FIG. 14, the wheel axes 756 may be within a range of perpendicular to the central axis 696, such as about 10 degrees to about 20 degrees. The angle may be toward the front 100*f* or toward the rear or control console 100*c*. As illustrated in FIG. 14, therefore, the angle 764 may be about 70° to about 90°, further including about 70° to about 88°, and further including about 70° to about 80°.

The angle 764 may allow the efficiency of driving the cart 100 generally in the direction of the double headed arrow 696 along the axis 673 to be similar to the cosine of the angle 764. Similarly, the angle of the axis 756 relative to the movement direction shown by the double headed arrow 696 may also be based upon an angle of the axis 756 to the axis. As illustrated in FIG. 13 and FIG. 14, the axis of rotation 756 of the wheels 742 is generally at the angle 764 relative to the long axis 673 of the base 103. The rollers 752, however, generally rotate on the axis 758 that is about 90° relative to the axis 756 of the wheel 742.

Each wheel assembly 742 may be driven independently by powering the motor 672, similar to the processes discussed above, to move the cart 100. As discussed above, the cart 100 may also be moved generally along the z-axis, such as in the direction of the arrows 696 including the axis 274, as illustrated in FIG. 4A, by driving the wheels 742. It is further understood that the gantry 48 may also move relative to the cart 100.

The wheel assemblies may be mounted to the base 103 with the mounting blocks 678 in a manner similar to that discussed above. For example the mounting blocks 678 may be fixed rigidly to the base 103. The base 103, however, may have a selected flexibility such that one or more of the wheels may go over a projection or depression, as discussed above, relative to a substantially flat portion of the support surface while allowing all of the four wheel assemblies 742 to remain in contact with the support surface. Accordingly, the cart 100 may be moved from a first location to another second location while maintaining the stability of the imaging system 20 and/or allowing the imaging system 20 to be transported over imperfections in a support surface.

Further the positioning of the wheel assemblies 742 at the corners of the base 103, is illustrated in FIG. 13 and FIG. 14, allows the imaging system 20 to be maintained substantially stable even on an incline. For example, the imaging system 20 may be positioned on an incline, such as a ramp, and be stable at any position of the gantry 48 relative to the cart 100 when the incline is 15 degrees or less, including about 10 degrees or less. Generally, the center of gravity of the imaging system 20 remains within the geometry defined by the wheels 742 to assist in maintaining stability of the imaging system 20 during positioning and transportation of the imaging system 20.

Also the positioning of the wheel assembly 742 to rotate around the respective axis 756 at an angle relative to the central axis 673 of the base 103 may allow for an efficient movement of the imaging device 20. As discussed above, the movement of the imaging device 20 in substantially any direction may cause for a force vector of the rollers 752 to be at an angle relative to the direction of travel. However, the angle of the axis 756 relative to the central axis 673 of the base 103 may cause the resistance to be the cosine of the angle 764 which is generally about 22% less efficient than if the wheels were solid wheels that rotate about an axis perpendicular to the long axis 673 and in the direction of travel of the cart 100.

Figure 15:
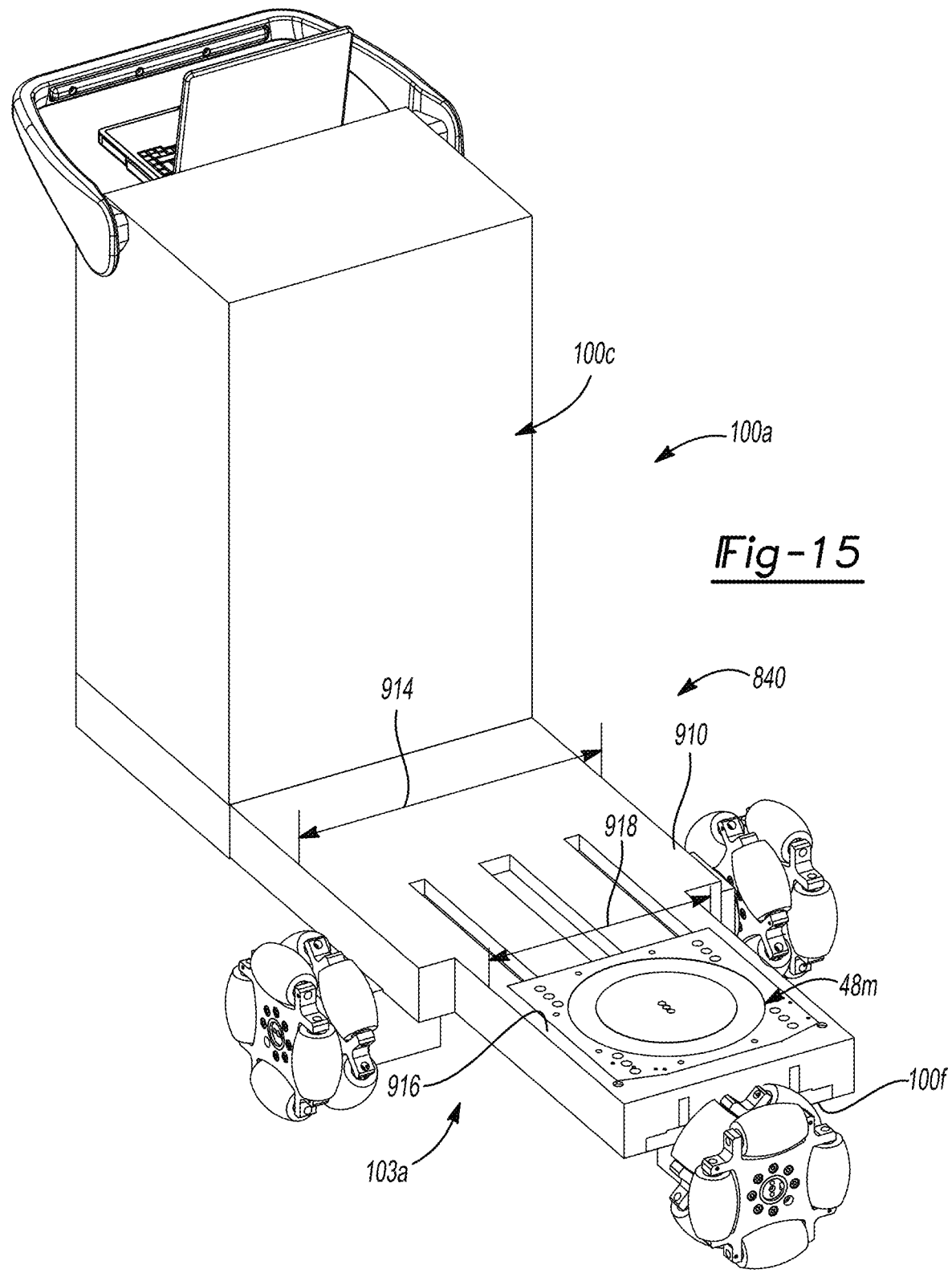
FIG. 15 is a top perspective view of a cart for an imaging system, according to various embodiments.
Figure 16:
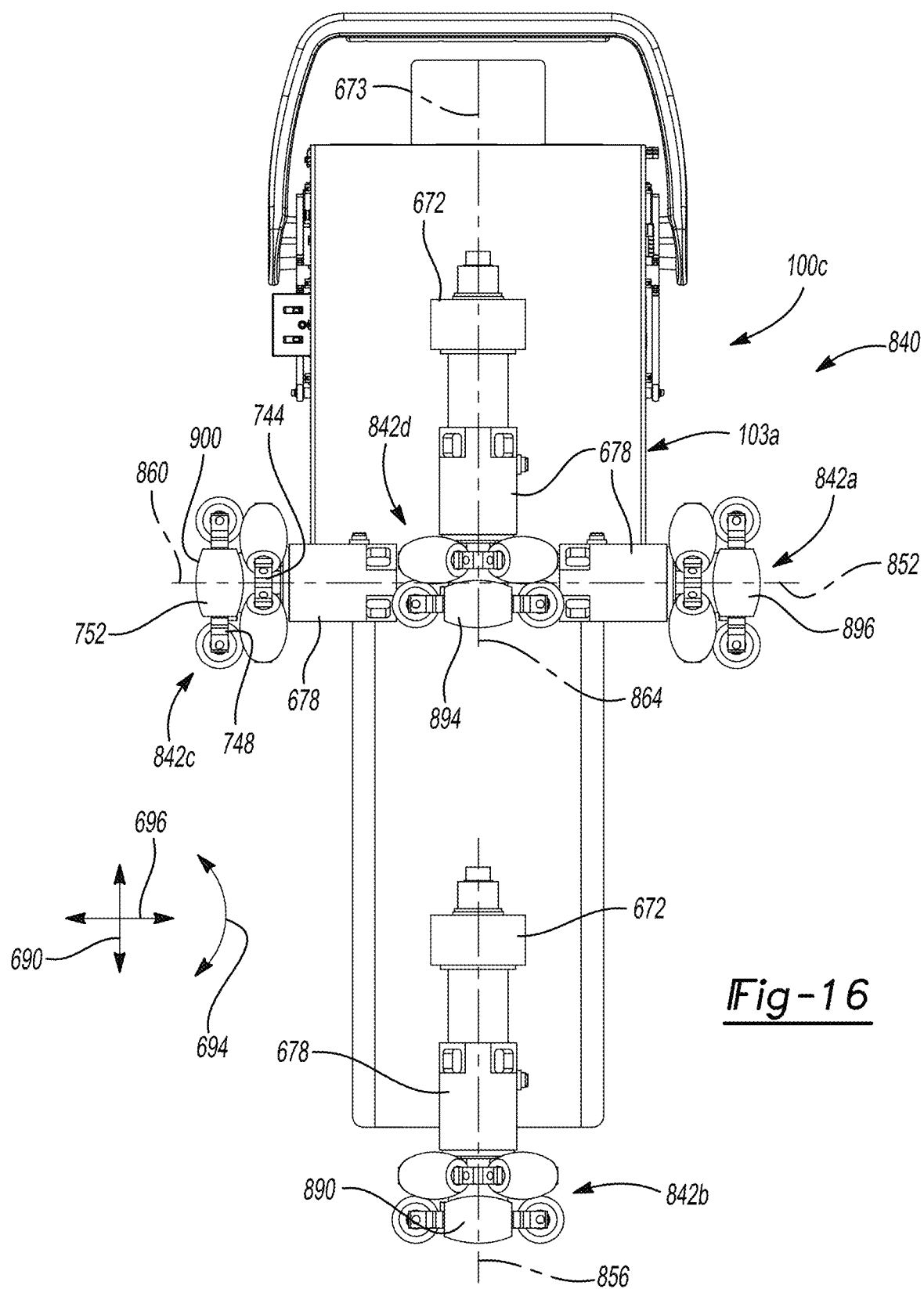
FIG. 16 is a bottom plan view of the cart of FIG. 15.

With reference to FIG. 15 and FIG. 16, a drive system 840 is illustrated for the imaging assembly 20. Similar to FIG. 13 and FIG. 14, however, the gantry 48 is not illustrated relative to the cart 100, however, the control portion 100*c* is illustrated as is a forward or front portion 100*f*. The drive system 840 includes a selected number of wheels 842, including four wheels referred to herein 842*a*, 842*b*, 842*c*, and 842*d*. The wheels 842 may be substantially similar to the wheels 742, illustrated in FIG. 14, save for their positioning relative to the base 103. The wheels, therefore, have hubs 744, 748 and rollers 752. The rollers 752 generally rotate in the same geometry relative to the hubs 744, 748 and manner as discussed above as to the wheels 842 rotate like the wheels 742.

The wheels 842 are connected to the base 103 with mounting block 678 and may be driven by motors 672. Further, each of the wheels may rotate around selected axes extending through the respective mounting blocks 678 including respective axis 852 for wheel assembly 842*a*, axis 856 for the wheel assembly 842*b*, axis 860 for the wheel assembly 842*c*, and axis 864 for the wheel assembly 842*d*.

The wheel assemblies 842 operate in a similar manner as the wheel assemblies 742 discussed above. However, as illustrated in FIG. 16, the central axis or axis of rotation 852 and 860 are substantially identical such that the wheel 842*a* and the wheel 842*c* rotate around the same axis that is generally perpendicular to the long axis 673 of the base 103. The two wheels 842*a*, 842*c*, however, may drive the cart 100 generally in the direction of the double-headed arrow 690 with only the two wheels 842*a* and 842*c* while the rollers 890 on the wheel 842*b* and rollers 894 on the wheel 842*d* rotate freely on the respective wheels 842*b*, 842*d*.

In a similar manner, when moving the cart 100 in the direction along the axis of the double headed arrow 696 the two wheels 842*d* and 842*b* may be powered and rollers 896 and 900 of the wheels 842*a*, 842*c* respectively, may rotate freely. The axes 856, 864 may generally be aligned or parallel with the long axis 673 of the base 103. The wheels 842*b*, 842*d*, therefore, may rotate around the respective axes to the move the base 103 in a direction generally orthogonal to the long axis 673.

Accordingly, the wheel drive assembly 840 may generally move the cart 100 along the two orthogonal axes by driving only two of the wheel assemblies at a time, alternatively. Further, the wheel assemblies may be powered to rotate to the cart 100 generally in the direction of the double headed arrow 694. Thus, less than all of the wheels may be powered to move the cart 100 in selected directions, such as along a line aligned with the long axis 673 or one orthogonal to the long axis 673.

As discussed above, the mounting structure 678 may be fixed to the base 103 in a substantially rigid manner. However, contact of all four of the wheels may be maintained with a support surface, such as a floor, even over bumps or depressions therein, due to flexibility of the base 103, as discussed above.

The base 103 may not be a single uniform size, however, as illustrated in FIG. 15 and FIG. 16. For example, as illustrated in FIG. 15 the base 103 may include a first portion 910 that has a first dimension, such as a width 914. The base 103 may further include a second portion 916 that has a second dimension, such as a width 918. The second width 918 may be less than the first width 914 or the respective dimension, of the respective portion 916, 914 of the base 103. The second portion of the base 916 nearer the front portion 100*f* may have a smaller width that may be great enough to hold or allow mounting of the gantry mount 48*m*, but need not be as wide as the first portion 910 of the base 103. Accordingly, a user, such as the surgeon 69, may move closer to the subject 40 and the gantry 48 when not obstructed by a portion of the base 103.

Further, the orientation and configuration of the drive assembly 40, as illustrated in FIG. 16, may define a plane having substantially three points defined by the first wheel 842*a*, the second wheel 842*b*, and the third wheel 842*c*. The fourth wheel 842*d* is generally along the line between the first wheel 842*a* and the third wheel 842*c*. The generally triangular configuration of the drive assembly 840, included in contact of the wheel assemblies 842 with a support surface, such as a floor, may allow for maneuvering of the cart 100 in small or tight spaces, such as around corners and/or doorways. Further the generally triangular configuration allows for the user 69 to place feet or legs near the gantry and the cart 100 when the second portion 916 of the base 103 is formed as narrowly as possible. By aligning the wheel assembly 842*b* to rotate around the axis 856 that is generally along a long axis defined by the double headed arrow 690 of the cart 100. The configuration of the drive assembly 840, however, may still maintain stability of the imaging system 20 in selected configurations of the gantry 48 relative to the base 103 even when on inclines of 15 degrees, including about 10 degrees or less.

Figure 17:
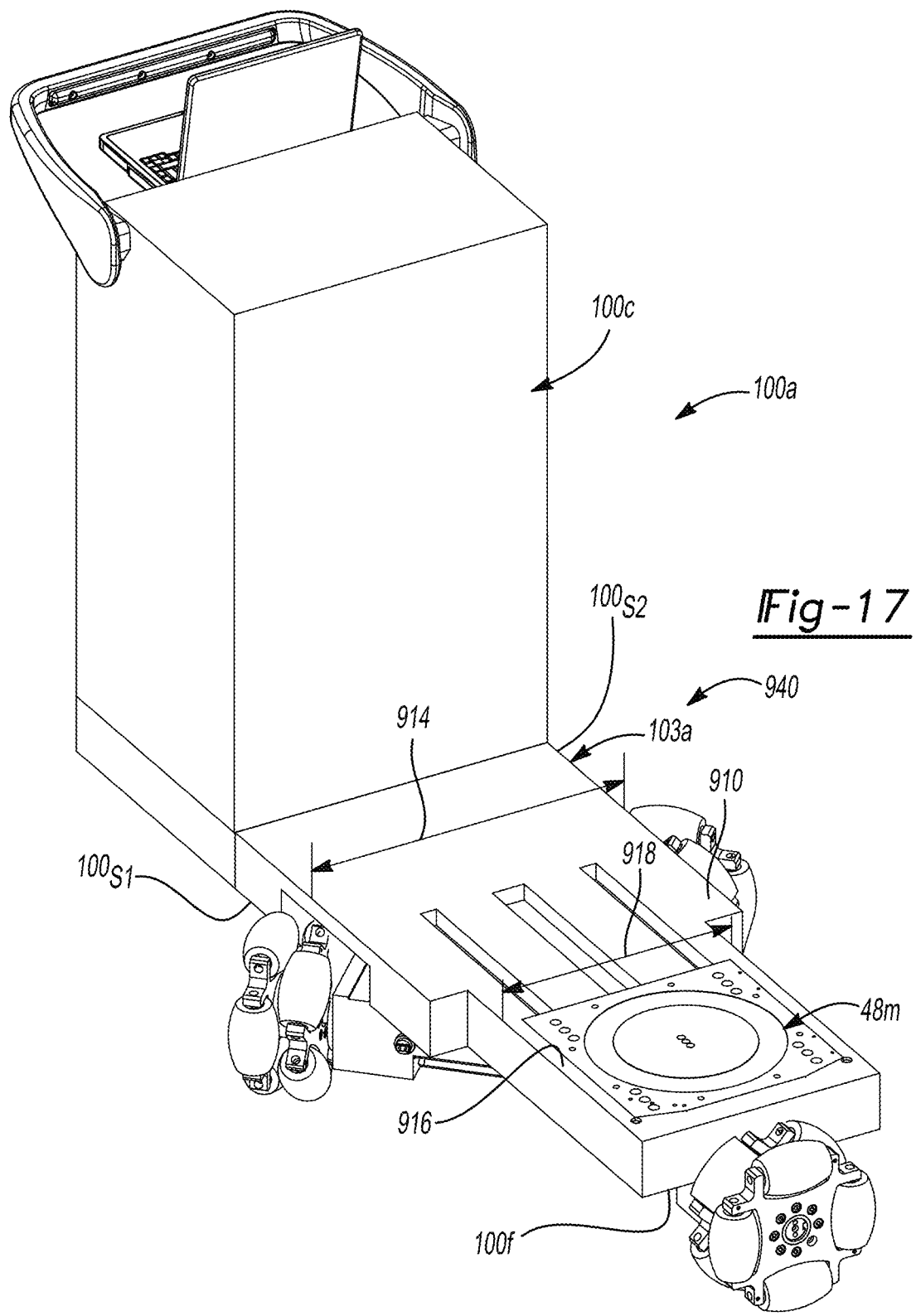
FIG. 17 is a top perspective view of a cart for an imaging system, according to various embodiments.
Figure 18:
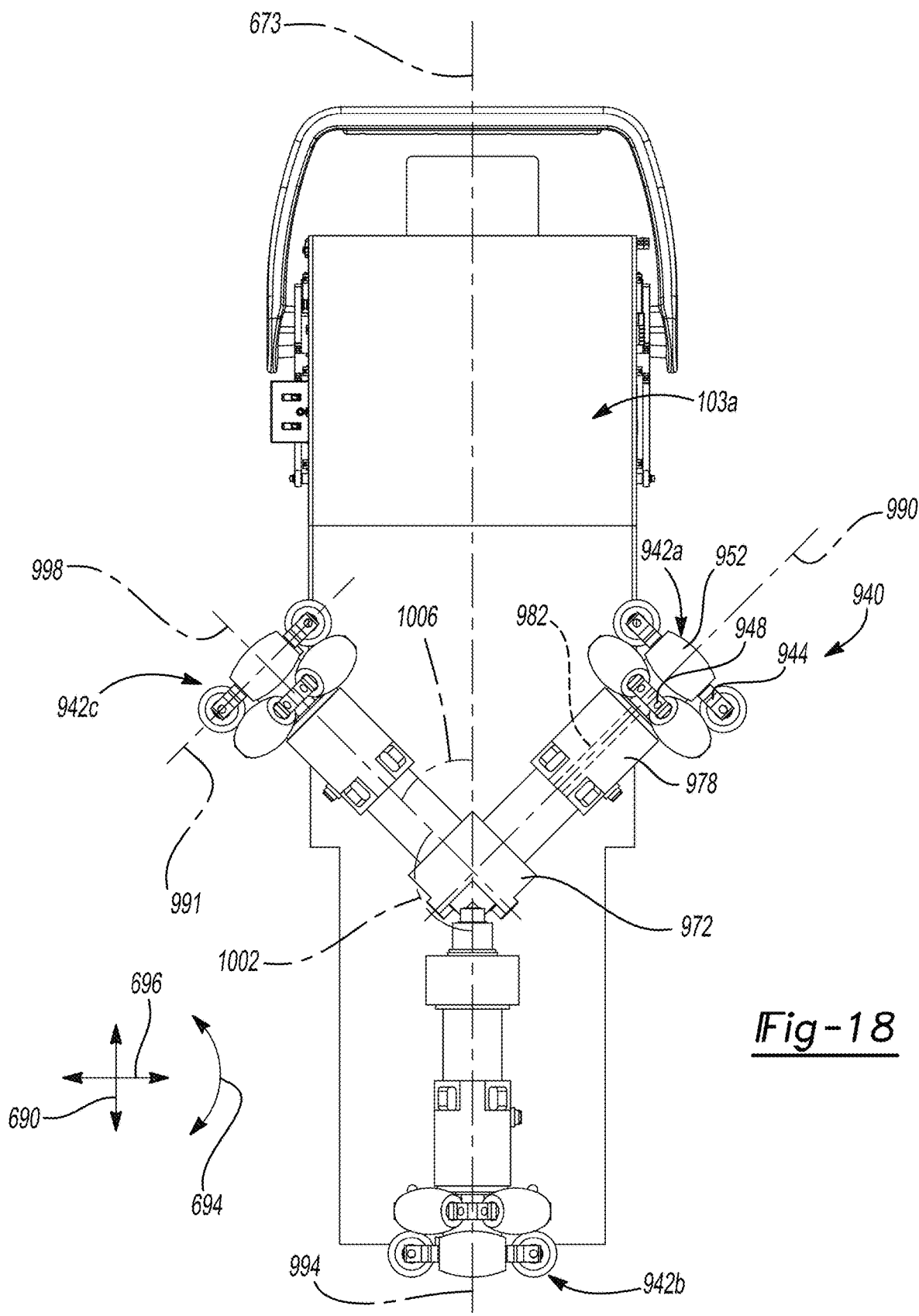
FIG. 18 is a bottom plan view of the cart of FIG. 17.

Turning, reference to FIG. 17 and FIG. 18, a drive assembly 940 is illustrated. The drive assembly 940 may be mounted on the base 103 of the cart 100 that extends from near the portion with the control 100*c* to the front 100*f* in between to side 100*s*1 and 100*s*2. The drive assembly may include wheel assemblies 942, such as three wheel assemblies 942*a*, 942*b*, and 942*c*.

Each of the wheel assemblies may include two hub members 944 and 948 similar to the wheel assembly 742 and hubs 744, 748 discussed above. Further, each of the hubs may have a plurality of rollers 952 rotatably mounted thereon. The wheel assemblies 942 are similar to the wheel assemblies 742, discussed above, including the individual configuration and geometries and will not be discussed in detail here. Each of the wheel assemblies are rigidly mounted to the base 103 with a mounting block 978 and may be driven by a motor 972. If selected, a gearing or transmission mechanism may also be provided between the motor 972 and the respective wheels 942. Further, each of the wheels 942 may rotate on an axle 982. The axle 982 may define an axis 990 around which the hubs 944, 948 rotate, causing the wheel assembly 942 to rotate around the axis 990 when driven by the motor 972. As discussed above, the rollers 952 may rotate around an axis 991 that is about 90 degrees relative to the wheel axis 990.

Each of the wheel assemblies of the drive assembly 940 rotate around a respective axis, therefore the wheel assembly 942*a* rotates around the axis 990, the wheel assembly 942*b* rotates around the axis 994, and the wheel assembly 942*c* rotates around the axis 998. The axes 990, 994, 998 may be positioned at an angle relative to one another that may substantially equal, such as about 120 degrees apart, or at any appropriate selected angle. Thus, an angle 1002 is formed between each of the axes. The cart base 103 may have the longitudinal axis 673 which may generally be in line with the double headed arrow 690 generally the direction from the front to the back of the cart 100. The wheel assemblies may have one axis, such as the axis 994 of the wheel assembly 942*b* that is substantially aligned or in line with the long axis 673. The other two axes 990, 998 may be formed at an angle relative to the long axis 673 such as that the angle 1006 may be about 40 degrees to about 80 degrees, including about 60 degrees. Thus, when the cart 100 moves in any direction, such as in the direction of the double headed arrow 690, none of the wheel assemblies roll freely. When the cart 100 moves in the direction of the double headed arrow 696 only the wheel assembly 942*b* rotates in a direction of rotation. Thus, the drive assembly 940 may have a force vector at the roller that is not in line with the direction of movement for movement of the cart 100, in most directions. Nevertheless, only three wheel assemblies of the drive assembly 940 are provided thus reducing contact and friction with the surface during movement of the cart 100.

Further the base 103 may be formed of a flexible material to allow for maintaining contact of all of the wheel assemblies 942 with a support surface, even when the support surface includes irregularities or projections or depressions, as discussed above. The wheels 942 may be spaced a distance apart, such as an appropriate distance, to maintain a stability of the cart 100.

In various embodiments, however, as illustrated in FIG. 18, the wheel assemblies 942 may only project partially from or past the sides 100*s*1, 100*s*2 to allow for driving of the cart 100. Moreover, the base 103 may include the two sections 910 and 916 that have the differing widths 914, 918, similar to the cart 100*a* and base 103*a*, discussed above. Thus, the second section 916 that is positioned to accept the mount 48*m* of the gantry may be narrower in the width 918 than the width 914 of the first section 910. As discussed above, this allows the surgeon 69 to move closer to the gantry and/or the patient 40 during a selected procedure. Again this also may be provided by positioning the axis of rotation 994 of the wheel assembly 942*b* to be in line with the long axis 673 of the cart 100. Also, the cart 100 may still remain stable in various configurations of the gantry 48 relative to the cart 100*a*. Further, the drive assembly 940 may be operated to move the gantry 48 in selected axis or axes for imaging, such as the Z-axis and the gantry 48 may not move relative to the cart 100*a* in the Z-axis.

As discussed above, the drive assemblies, such as the drive assembly 340, 640, 740, 840, and 940 may all be provided to include wheel assemblies that allow for multi-directional movement of the cart 100 without rotating the wheel assemblies relative to the cart. Selected types or configurations of wheels may include mecanum and/or omni-directional wheels, as discussed above. The wheel designs may also be selected to achieve the selected movement of the cart based upon movement control of the wheels. Further, an appropriate number of wheels may include more than 4 wheel assemblies or less than 3 wheel assemblies, according to various embodiments.

These wheels allow for movement of the cart 100 in substantially orthogonal and directions and rotation around a point without twisting or rotating the wheels relative to the cart 100. Thus the cart 100 may move in orthogonal axes without rotating wheel assemblies, such as rotating caster wheels. Thus, as discussed above and illustrated in FIGS. 4A and 4B, the cart 100 may be used to move the gantry 48 in a Z-axis for acquiring image data of the subject 40. The gantry 48 may move relative to the cart in a Z-axis, according to various embodiments. According to various embodiments, however, the cart 100 may move in a Z-axis in addition to the gantry 48 also moving relative to the cart 100 in the Z-axis. Further it is understood, however, that the gantry 48 may be fixed to the cart 100 and the cart 100 moves in the Z-axis rather than the gantry 48. This allows the imaging system 20 to include a Z-axis movement or movement along the axis 274, as illustrated in FIG. 1, that is due to movement of the gantry 48 relative to the cart 100 alone, movement of the gantry 48 relative to the cart in combination with movement of the cart, or only movement of the cart 100 to move the gantry 48 while the gantry 48 remains fixed relative to the cart.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to acquire image data of a subject, comprising:
   a cart having a support structure and a base;
   a detector configured to detect an emitted energy, wherein the detection of the emitted energy is operable to be image data;
   a gantry defining an interior enclosed space, wherein the detector is configured to move within the interior enclosed space defined by the gantry, wherein the gantry extends away from the support structure and over a surface; and
   a multi-directional drive system including at least one omni-directional wheel and at least one motor to drive the at least one omni-directional wheel;
   wherein the multi-directional drive system is operable to receive an input to move the cart within a plane on the surface.

2. The system of claim 1, wherein the multi-directional drive system includes at least one moveable support configured to allow movement of the cart in at least two axes substantially simultaneously.

3. The system of claim 2, wherein the at least one moveable support includes at least one omni-directional wheel; and
   wherein the multi-directional drive system includes at least one motor to drive the at least one omni-directional wheel.

4. The system of claim 3, wherein the at least one omni-directional wheel includes a plurality of rollers configured to allow the at least one omni-directional wheel to translate in a plane or rotate around an axis.

5. The system of claim 3, wherein the multi-directional drive system includes a first multi-directional drive sub-system and a second multi-directional drive sub-system.

6. The system of claim 5, wherein the at least one omni-directional wheel includes a plurality of omni-directional wheels;
   wherein the first multi-directional drive sub-system includes at least a first omni-directional wheel and a second omni-directional wheel of the plurality of omni-directional wheels;
   wherein the second multi-directional drive sub-system includes a third omni-directional wheel and a fourth omni-directional wheel of the plurality of omni-directional wheels.

7. The system of claim 6, wherein each of the first omni-directional wheel, the second omni-directional wheel, the third omni-directional wheel, and the fourth omni-directional wheel is positioned near a corner of a support base defined by the multi-directional drive system.

8. The system of claim 6, further comprising:
   a first motor coupled to the first omni-directional wheel to drive the first omni-directional wheel;
   a second motor coupled to the second omni-directional wheel to drive the second omni-directional wheel;
   a third motor coupled to the third omni-directional wheel to drive the third omni-directional wheel; and
   a fourth motor coupled to the fourth omni-directional wheel to drive the fourth omni-directional wheel.

9. The system of claim 3, wherein the at least one omni-directional wheel includes a first omni-directional wheel, a second omni-directional wheel, a third omni-directional wheel, and a fourth omni-directional wheel;
   wherein each of the first omni-directional wheel, the second omni-directional wheel, the third omni-directional wheel, and the fourth omni-directional wheel are operable to be driven independently of each other omni-directional wheel to rotate the cart and translate the cart in a plane.

10. The system of claim 1, further comprising a movement control assembly, including:
    a handle configured to be engaged by a user;
    a sensor to sense a force applied by the user and a direction of the force; and
    a movement control configured to receive a signal from the sensor based on the sensed force and generate a drive signal to drive the multi-directional drive system to all of (i) rotate the cart and (ii) translate the cart in the plane relative to the surface and the subject.

11. The system of claim 1, further comprising:
    a sensor configured to sense a change in location of all of the detector, the gantry, the cart, or combinations thereof during an image data acquisition;
    wherein the sensor is configured to generate a location signal regarding the change in location.

12. The system of claim 11, further comprising:
    an imaging processor configured to generate an image based on the image data and the location signal from the sensor.

13. The system of claim 12, further comprising:
    a movement control system to automatically determine a signal that is received as the input by the multi-directional drive system to move at least the cart to acquire the image data.

14. A system to acquire image data of a subject, comprising:
    an image data collection system;
    a cart having a support structure and a base;
    a gantry defining an interior space that encloses the image data collection system as the image data collection system moves relative to the subject, wherein the gantry extends from the support structure and above a surface; and a multi-directional drive system mounted to the base including a plurality of omni-directional wheels and at least one motor to drive the plurality of omni-directional wheels; and a movement control system having an input system to receive an input from a user to control the multi-directional drive system;

wherein the multi-directional drive system is operable to receive an input to move the cart on the surface within a plane.

15. The system of claim 14, wherein the multi-directional drive system includes a first frame member and a second frame member;

wherein the first frame member is moveable relative to the second frame member;

wherein both the first frame member and the second frame member are moveable relative to the base.

16. The system of claim 14, wherein the movement control assembly includes:

a handle configured to be engaged by the user;

a sensor to sense a force applied by the user and a direction of the force; and a movement control configured to receive a signal from the sensor based on the sensed force and generate a drive signal to drive the multi-directional drive system to all of (i) rotate the cart and (ii) translate the cart in a plane.

17. The system of claim 14, wherein the plurality of omni-directional wheels includes three omni-directional wheels that rotate around respective axes that intersect.

18. The system of claim 14, wherein the plurality of omni-directional wheels includes four omni-directional wheels that rotate around respective axes;

wherein at least one pair of the respective axes intersect.

19. A method of moving an imaging system to acquire image data of a subject, comprising:

providing an image data collection system to be enclosed within a gantry;

providing the gantry supported by a cart having a support structure and a base, wherein the support structure is configured to hold the gantry away from a surface; and operating a movement control system to automatically determine movement of the imaging system to acquire image data of the subject;

controlling a multi-directional drive system that is mounted to the base with a signal from the movement control system;

wherein the multi-directional drive system includes a plurality of omni-directional wheels and at least one motor to drive the plurality of omni-directional wheels;

wherein the plurality of omni-directional wheels move the case on the surface.

20. The method of claim 19, further comprising:

applying a force to a handle assembly;

operating a sensor to sense the force; and receiving a sense signal from the sensor to move the imaging system in at least one of six-degrees of freedom.

* * * * *

UNITED STATES PATENT AND TRADEMARK OFFICE
CERTIFICATE OF CORRECTION

PATENT NO. : 11,925,494 B2
APPLICATION NO. : 17/740534
DATED : March 12, 2024
INVENTOR(S) : David A. Garlow et al.

Page 1 of 1

It is certified that error appears in the above-identified patent and that said Letters Patent is hereby corrected as shown below:

In the Specification

Column 6, Detailed Description, Line 17, Delete "30" and insert --20-- therefor

Column 10, Detailed Description, Line 30, Delete "200." and insert --20.-- therefor Column 13, Detailed Description, Line 12, Delete "220" and insert --20-- therefor Column 14, Detailed Description, Line 7, After "110", insert --.--

Column 18, Detailed Description, Line 65, Delete "286" and insert --268-- therefor Column 20, Detailed Description, Line 24, Delete "642." and insert --652.-- therefor Column 21, Detailed Description, Line 5, Delete "670" and insert --673-- therefor Column 21, Detailed Description, Line 6, Delete "103" and insert --100-- therefor Column 21, Detailed Description, Line 53, Delete "103." and insert --100.-- therefor Column 22, Detailed Description, Line 67, Delete "103." and insert --100.-- therefor Column 25, Detailed Description, Line 6, Delete "40," and insert --840,-- therefor Signed and Sealed this
Twenty-fifth Day of February, 2025

Coke Morgan Stewart
*Acting Director of the United States Patent and Trademark Office*